(12) United States Patent
Schmitt

(10) Patent No.: US 12,310,803 B2
(45) Date of Patent: May 27, 2025

(54) FUNCTIONAL INDICATORS FOR ROBOTIC MEDICAL SYSTEMS

(71) Applicant: Auris Health, Inc., Redwood City, CA (US)

(72) Inventor: Fabien Y. Schmitt, Redwood City, CA (US)

(73) Assignee: Auris Health, Inc., Santa Clara, CA (US)

( * ) Notice: Subject to any disclaimer, the term of this patent is extended or adjusted under 35 U.S.C. 154(b) by 1026 days.

(21) Appl. No.: 17/127,007

(22) Filed: Dec. 18, 2020

(65) Prior Publication Data

US 2021/0186644 A1 Jun. 24, 2021

Related U.S. Application Data

(60) Provisional application No. 62/951,799, filed on Dec. 20, 2019.

(51) Int. Cl.
| | | |
|---|---|---|
| *A61B 34/30* | (2016.01) | |
| *A61B 34/37* | (2016.01) | |
| *A61B 90/50* | (2016.01) | |
| A61B 90/00 | (2016.01) | |
| A61B 90/30 | (2016.01) | |

(52) U.S. Cl.
CPC ............. *A61B 90/50* (2016.02); *A61B 34/30* (2016.02); *A61B 2034/301* (2016.02); *A61B 34/37* (2016.02); *A61B 2090/0807* (2016.02); *A61B 2090/309* (2016.02)

(58) Field of Classification Search
CPC ............... A61B 34/30–77; B25J 19/00; B25J 19/02–068; B25J 9/0009; B25J 9/0096; B25J 9/1674; B25J 9/1694
See application file for complete search history.

(56) References Cited

U.S. PATENT DOCUMENTS

| | | |
|---|---|---|
| 8,100,133 B2 | 1/2012 | Mintz et al. |
| 8,273,076 B2 | 9/2012 | Devengenzo et al. |
| 8,551,116 B2 | 10/2013 | Julian et al. |
| 8,894,634 B2 | 11/2014 | Devengenzo et al. |
| 9,763,741 B2 | 9/2017 | Alvarez et al. |
| 9,775,682 B2 | 10/2017 | Quaid et al. |
| 10,130,429 B1 | 11/2018 | Weir |
| 10,192,195 B1 * | 1/2019 | Brazeau ............... B25J 9/1661 |
| 10,258,416 B2 | 4/2019 | Mintz et al. |
| 2007/0005045 A1 | 1/2007 | Mintz et al. |

(Continued)

FOREIGN PATENT DOCUMENTS

| WO | WO-2019100759 A1 * | 5/2019 | ............ B25J 9/0009 |
|---|---|---|---|

OTHER PUBLICATIONS

Office Action dated Feb. 9, 2024; U.S. Appl. No. 17/218,006, filed Mar. 30, 2021; 12 pages.

*Primary Examiner* — Carolyn A Pehlke
(74) *Attorney, Agent, or Firm* — Frost Brown Todd LLP

(57) ABSTRACT

A robotic medical system can include a patient platform configured to support a patient during a robotic medical procedure, a column supporting the patient platform, and an arm support coupled to the column with at least one robotic arm coupled to the arm support. The system can also include an indicator positioned on at least one of the arm support and the patient platform, wherein the indicator is configured to indicate state or identity information of the system. The indicator can be a visual indicator.

18 Claims, 28 Drawing Sheets

(56) References Cited

U.S. PATENT DOCUMENTS

| | | | |
|---|---|---|---|
| 2007/0048118 A1* | 3/2007 | Ogawa | B25J 5/007 |
| | | | 414/467 |
| 2012/0059390 A1 | 3/2012 | Mintz et al. | |
| 2015/0073437 A1 | 3/2015 | Devengenzo et al. | |
| 2017/0001315 A1* | 1/2017 | Katayama | B25J 19/06 |
| 2018/0078439 A1* | 3/2018 | Cagle | A61B 34/30 |
| 2018/0079090 A1* | 3/2018 | Koenig | G01L 3/14 |
| 2018/0168761 A1 | 6/2018 | Vargas et al. | |
| 2019/0216576 A1* | 7/2019 | Eyre | A61B 1/00149 |
| 2019/0231460 A1* | 8/2019 | DiMaio | B25J 9/1676 |
| 2020/0000536 A1* | 1/2020 | Yakimovich | B25J 13/085 |
| 2020/0253678 A1* | 8/2020 | Hulford | A61B 34/25 |
| 2022/0047329 A1 | 2/2022 | LaVallee et al. | |

* cited by examiner

FUNCTIONAL INDICATORS FOR ROBOTIC MEDICAL SYSTEMS

PRIORITY APPLICATION

This application claims priority to U.S. Provisional Application No. 62/951,799, filed Dec. 20, 2019, which is incorporated herein by reference. Any and all applications for which a foreign or domestic priority claim is identified in the Application Data Sheet as filed with the present application are hereby incorporated by reference under 37 CFR 1.57.

TECHNICAL FIELD

This application is directed to robotic medical systems, and more particularly, to functional indicators for robotic medical systems.

BACKGROUND

Medical procedures, such as laparoscopy or endoscopy, may involve accessing and visualizing an internal region of a patient. In a laparoscopic procedure, for example, a medical instrument can be inserted into an internal region through a laparoscopic access port. Robotically-enabled medical system can be used to perform such medical procedures. The robotically-enabled medical systems may include several robotic components, including, for example, robotic arms, robotic instrument manipulators, and robotic medical instruments, such as robotically controllable laparoscopes or endoscopes.

SUMMARY

Robotic medical systems that include one or more robotic components can also include functional indicators configured to communicate information about the system or its components. As initial examples, the functional indicators can comprise visual indicators (e.g., lights) and/or audible indicators (e.g., speakers). In some embodiments, the robotic medical systems can include one or more robotic arms positioned on adjustable arm supports configured to move to position the one or more robotic arm supports relative to a patient platform supporting a patient during a robotic medical procedure. The functional indicators can be positioned, for example, on the adjustable arm supports or a patient platform. The indicators can be configured, for example, to provide state and/or identity information associated with the system or its components. The indicators can also be used in non-robotic systems as well.

In a first aspect, a robotic medical system includes a patient platform configured to support a patient during a robotic medical procedure; a column supporting the patient platform; an arm support coupled to the column; at least one robotic arm coupled to the arm support; and an indicator positioned on at least one of the arm support and the patient platform, wherein the indicator is configured to indicate state or identity information of the system.

The system can include one or more of the following features in any combination: (a) wherein the indicator comprises at least one of a visual indicator and an audible indicator; (b) wherein the arm support comprises an adjustable arm support configured to move the at least one robotic arm relative to the patient platform; (c) wherein the adjustable arm support is configured to move the at least one robotic arm from a stowed position below the patient platform to a deployed position wherein at least a portion of the at least one robotic arm is positioned above the patient platform; (d) wherein the arm support comprises a bar extending along an axis between a first end and a second end, and wherein the at least one robotic arm is movably mounted to the bar such that the at least one robotic arm can translate along the bar; (e) wherein the indicator comprises a visual indicator; (f) wherein the visual indicator is positioned on at least one of a top side, an outer side, an inner side, and a bottom side of the bar; (g) wherein the visual indicator extends onto the first end and the second end of the bar; (h) wherein the visual indicator comprises a strip of light emitting diodes (LEDs); (i) wherein the state information comprises information about movement of at least one of the arm support and the at least one robotic arm; (j) wherein the state information indicates a direction of movement of the arm support; (k) wherein the direction of movement comprises a sweeping movement of the arm support; (l) wherein the direction of movement comprises a translating movement of the arm support; (m) wherein the state information indicates a direction of movement of the at least one robotic arm along the arm support; (n) wherein the state information comprises an identifier for the at least one robotic arm; (o) wherein the state information comprises first state information and second state information; (p) wherein the first state information comprises at least one of: a stand by state, a powered state, an active state, a ready state, an error state and an emergency stop state; (q) wherein the second state information is configured to indicate movement of the arm support; (r) wherein the visual indicator is configured to indicate the first state information and the second state information concurrently; and/or (s) wherein the visual indicator is configured to illuminate a zone around the system indicative of an area through which the arm support will move to provide a visual indication of a zone of danger.

In another aspect, a robotic medical system includes a patient platform configured to support a patient during a robotic medical procedure; a column supporting the patient platform; an adjustable arm support coupled to the column and configured to move relative to the patient platform, the adjustable arm support comprising a bar extending along an axis between a first end and a second end; a first robotic arm coupled to the bar of the adjustable arm support and configured to translate along the bar; a second robotic arm coupled to the bar of the adjustable arm support and configured to translate along the bar independently of the first robotic arm; and a light strip positioned on at least one of the patient platform and the bar of the adjustable arm support; and a processor in communication with a memory that stores instructions that configured the processor to: determine a state of the robotic medical system, and activate the light strip to convey the state of the robotic medical system visually.

The system can include one or more of the following features in any combination: (a) wherein the light strip comprises a strip of individually-addressable light emitting diodes (LEDs); (b) wherein the light strip is positioned on at least one of a top side, an outer side, inner side, and a bottom side of the bar; (c) wherein the light strip extends onto the first end and the second end of the bar; (d) wherein the state comprises a movement of the adjustable arm support, the first robotic arm, or the second robotic arm, and the processor is configured to activate the light strip to convey a direction of the movement; (e) wherein the movement comprises a translation of the bar of the adjustable arm support or a translation of one of the first robotic arm and the second robotic arm along the bar; (f) wherein the movement comprises a sweeping movement of the bar of the adjustable arm support; (g) wherein the processor determines the state of the robotic medical system based on a user input; (h) wherein the user input comprises a commanded motion for at least one of the first robotic arm and the second robotic arm; (i) wherein the user input comprises at least one of: a stow command for transitioning the adjustable arm support, the first robotic arm, and the second arm support from a deployed position to a stowed position; and a set up command for transitioning the adjustable arm support, the first robotic arm, and the second arm support from a stowed position to a deployed position; and/or (j) wherein upon receipt of the stow command, the system is configured to, at least one of: move the adjustable arm support and the first robotic arm to a draping configuration; and move the adjustable arm support and the first robotic arm to a pre-docking position.

In another aspect, a robotic medical system includes: a patient platform configured to support a patient during a robotic medical procedure; a column supporting the patient platform; an adjustable arm support coupled to the column and configured to move relative to the patient platform, the adjustable arm support comprising a bar extending along an axis between the first end and the second end; a first robotic arm coupled to the bar of the adjustable arm support and configured to translate along the bar; and a visual indicator positioned on the adjustable arm support or the patient platform and configured to visually identify the first robotic arm.

The system can include one or more of the following features in any combination: (a) wherein the visual indicator comprises a light strip, and wherein a portion of the light strip is configured to illuminate to identify the first robotic arm; (b) wherein the portion of the light strip that illuminates to identify the first robotic arm varies along the light strip as the first robotic arm translates along the bar; (c) wherein the light strip extends along the bar; (d) wherein the light strip extends along the patient platform; (e) a second robotic arm coupled to the bar of the adjustable arm support and configured to translate along the bar independently of the first robotic arm, and wherein the visual indicator is configured to visually identify the second robotic arm; (f) wherein the visual indicator uniquely identifies the first robotic arm and the second robotic arm; (g) wherein the visual indicator uniquely identifies the first robotic arm and the second robotic arm using different color lights; (h) wherein the visual indicator is positioned on at least one of a top side, an outer side, an inner side, and a bottom side of the bar; (i) wherein the visual indicator extends onto the first end and the second end of the bar; (j) wherein the visual indicator is configured provide information based on a state of the robotic system; (k) wherein the state information comprises information about movement of the arm support and the first robotic arm; (l) wherein the state information indicates a direction of movement of the arm support; (m) wherein the direction of movement comprises a sweeping movement of the arm support; (n) wherein the direction of movement comprises a translating movement of the arm support; (o) wherein the state information indicates a direction of movement of the first robotic arm along the arm support; (p) wherein the state information comprises an identifier for the first robotic arm; (q) where in the state information comprises first state information and second state information; (r) wherein the first state information comprises at least one of: a stand by state, a powered state, an active state, a ready state, an error state and an emergency stop state; (s) wherein the second state information is configured to indicate movement of the arm support; (t) wherein the visual indicator is configured to indicate the first state information and the second state information concurrently; and/or (u) wherein the visual indicator is configured to illuminate a zone around the system indicative of an area through which the arm support will move to provide a visual indication of a zone of danger.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 21A illustrates the system with adjustable arm supports and robotic arms in an example stowed position below a patient platform.

FIG. 21B illustrates the system with the adjustable arm supports and the robotic arm in an example deployed position.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
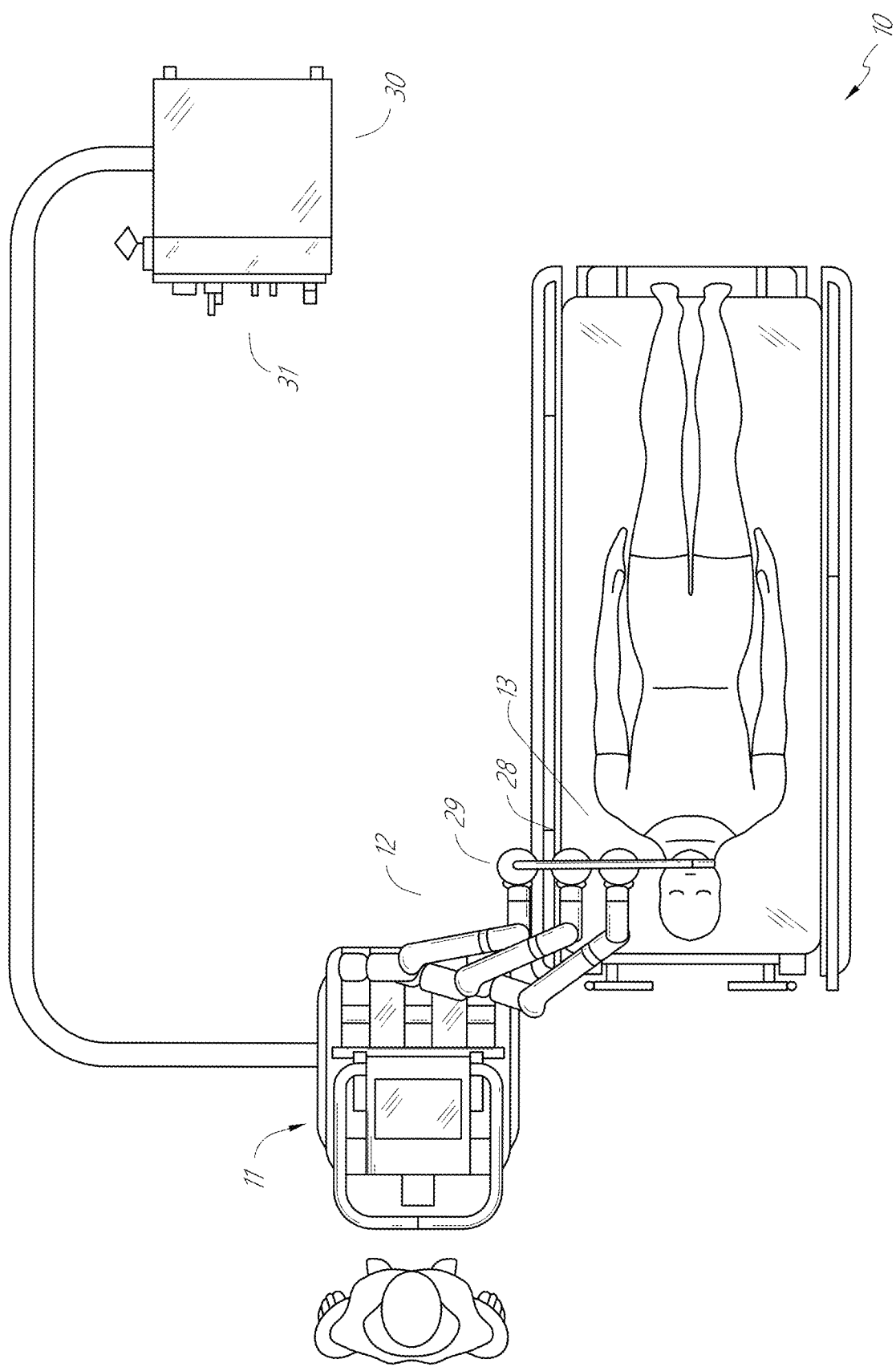
FIG. 1 illustrates an embodiment of a cart-based robotic system arranged for diagnostic and/or therapeutic bronchoscopy.
Figure 2:
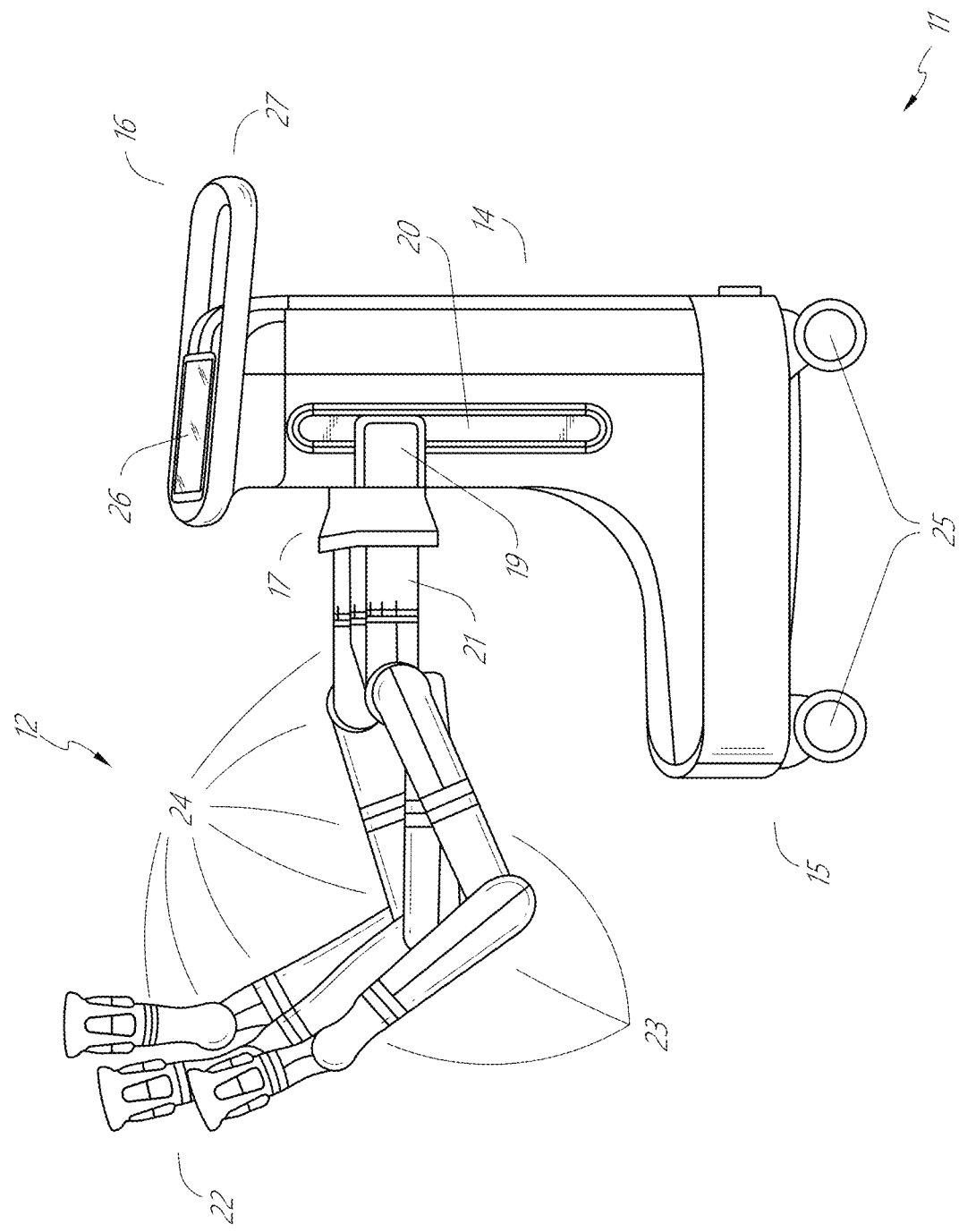
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
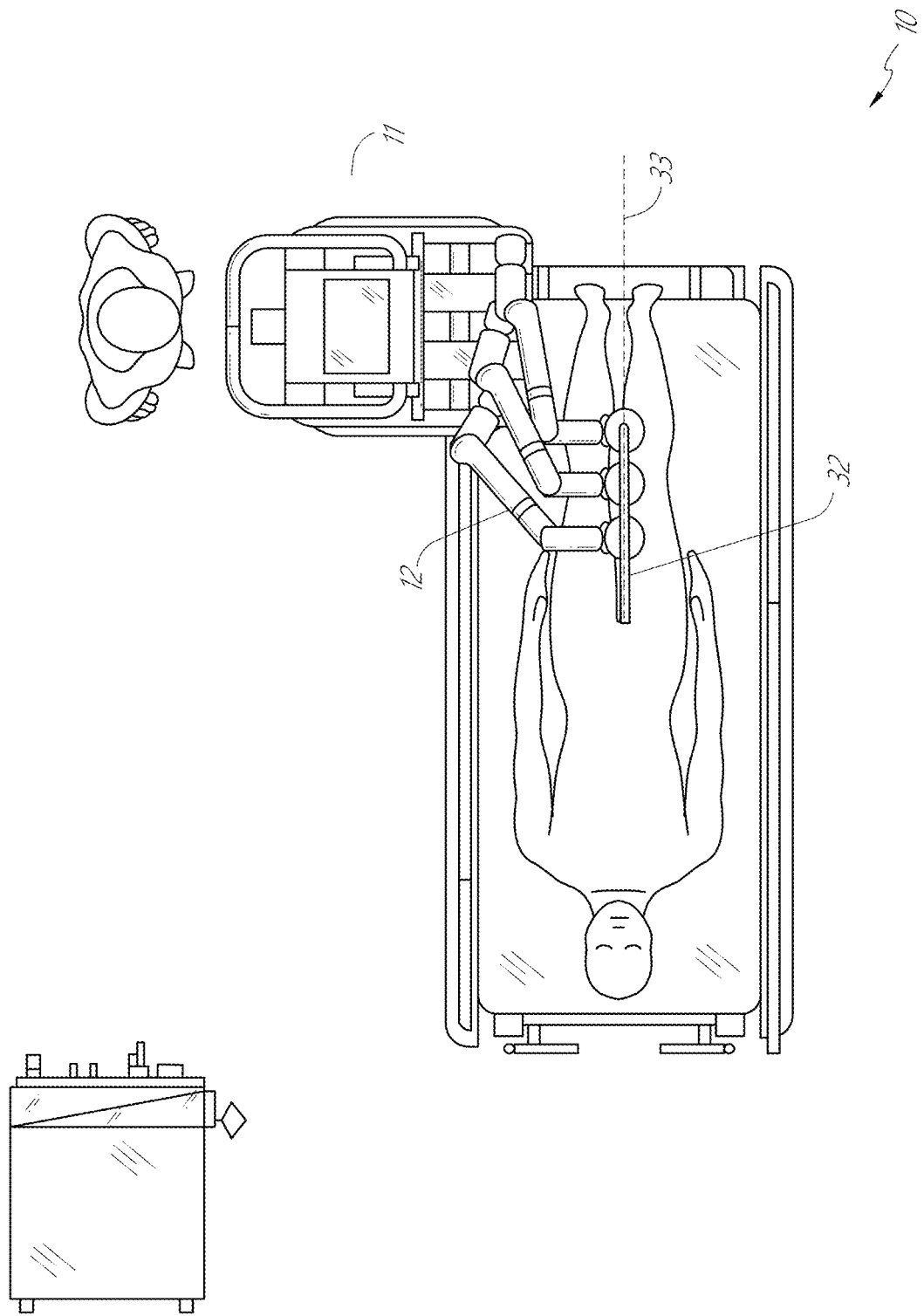
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
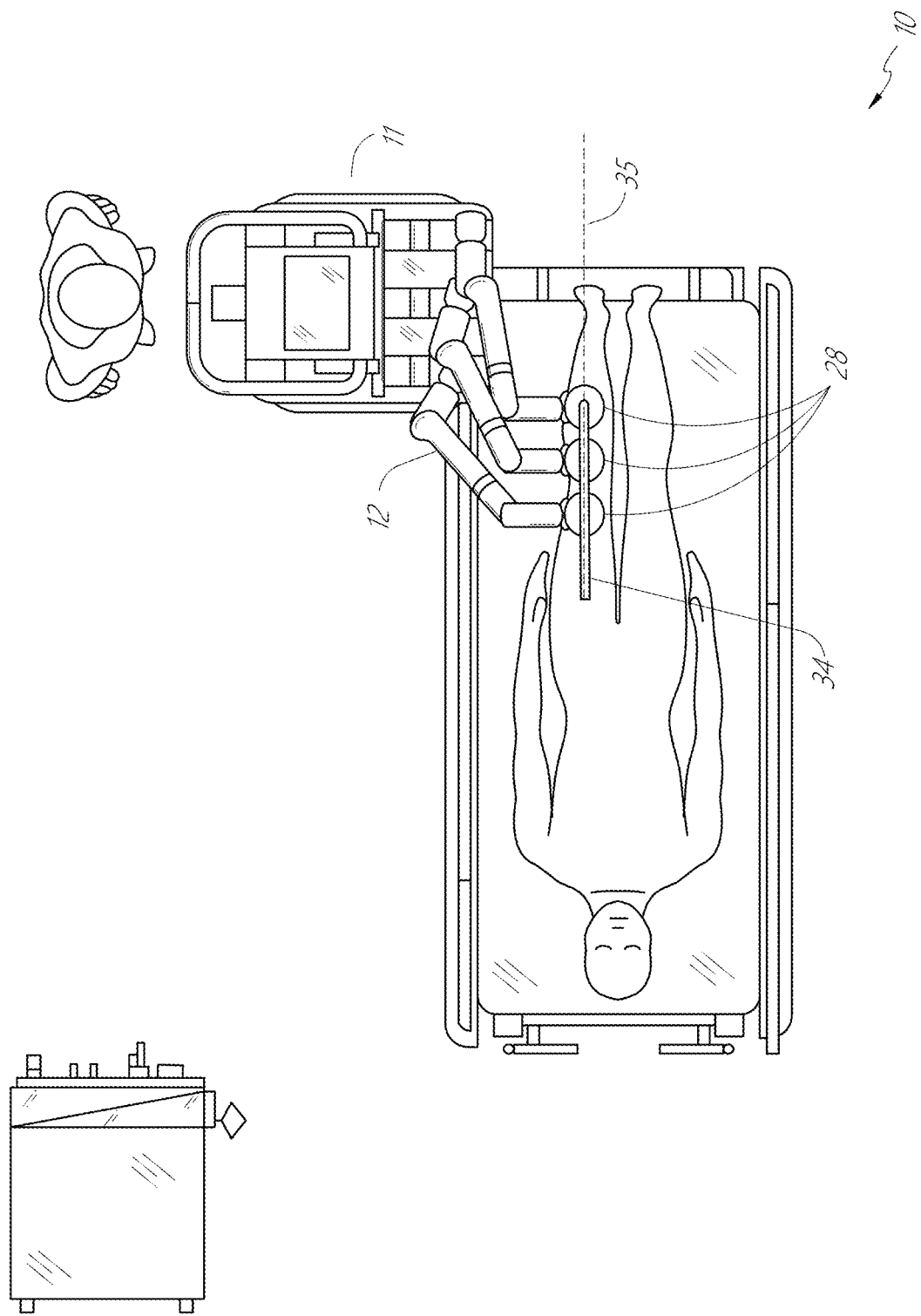
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
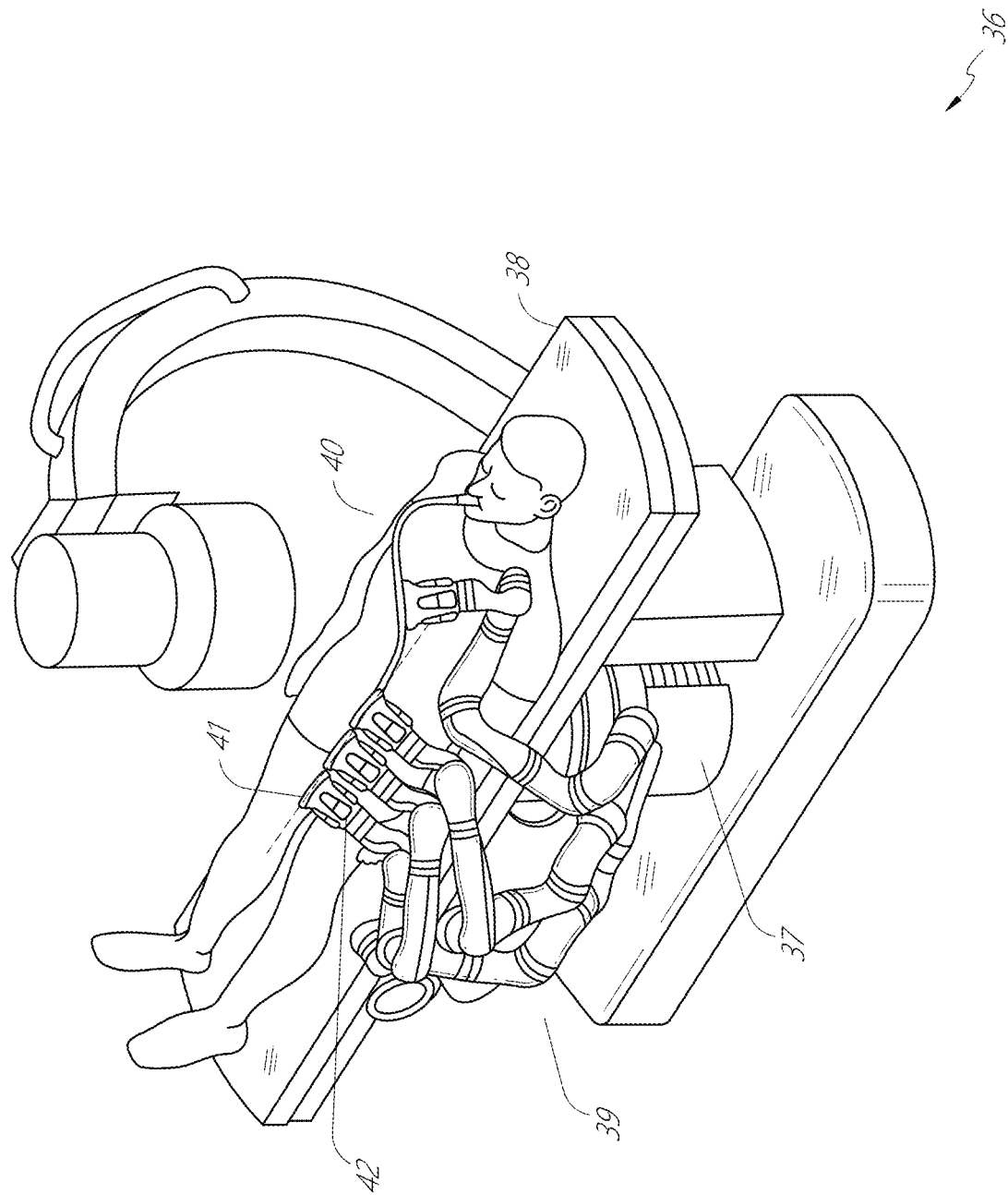
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
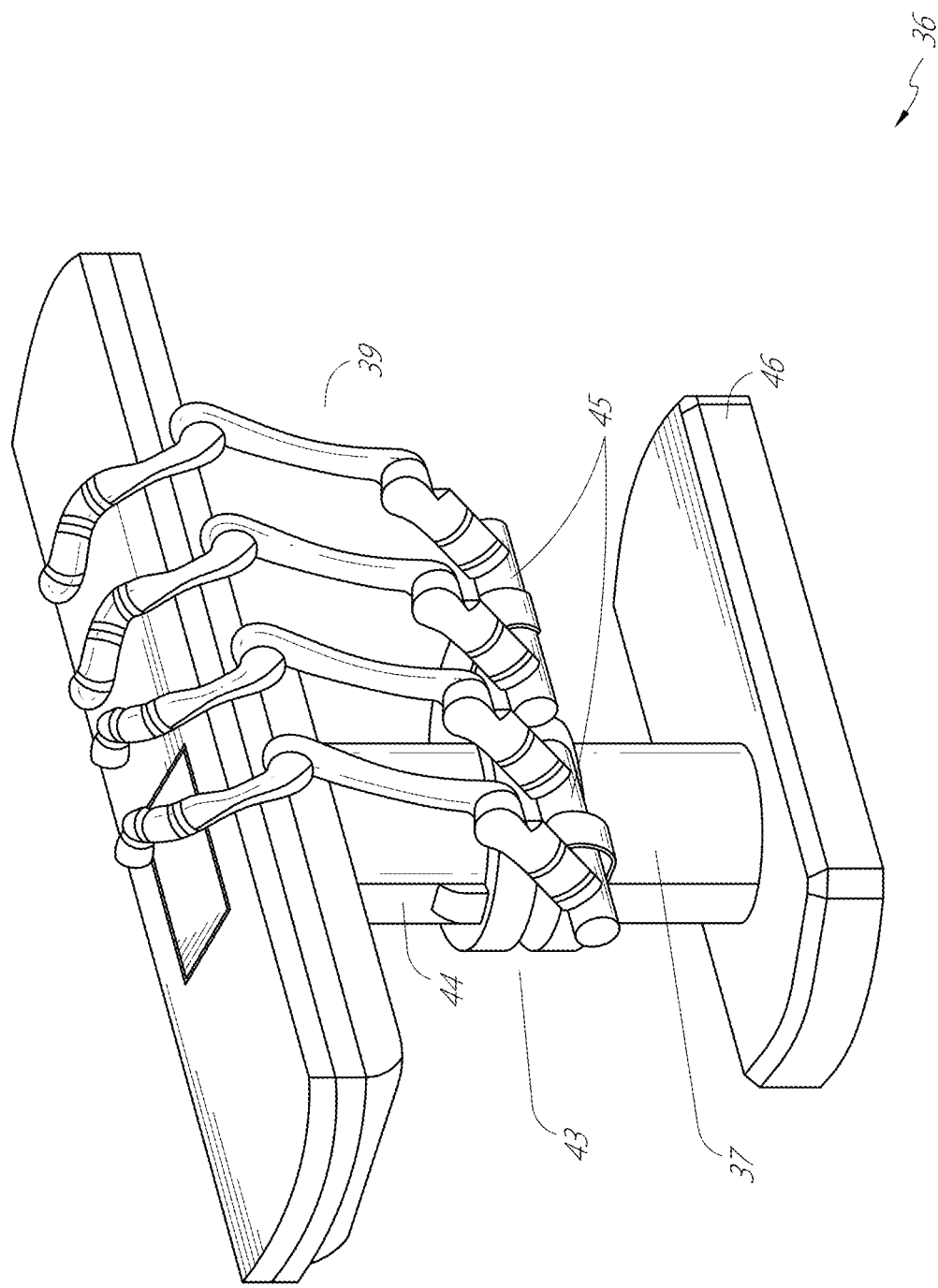
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
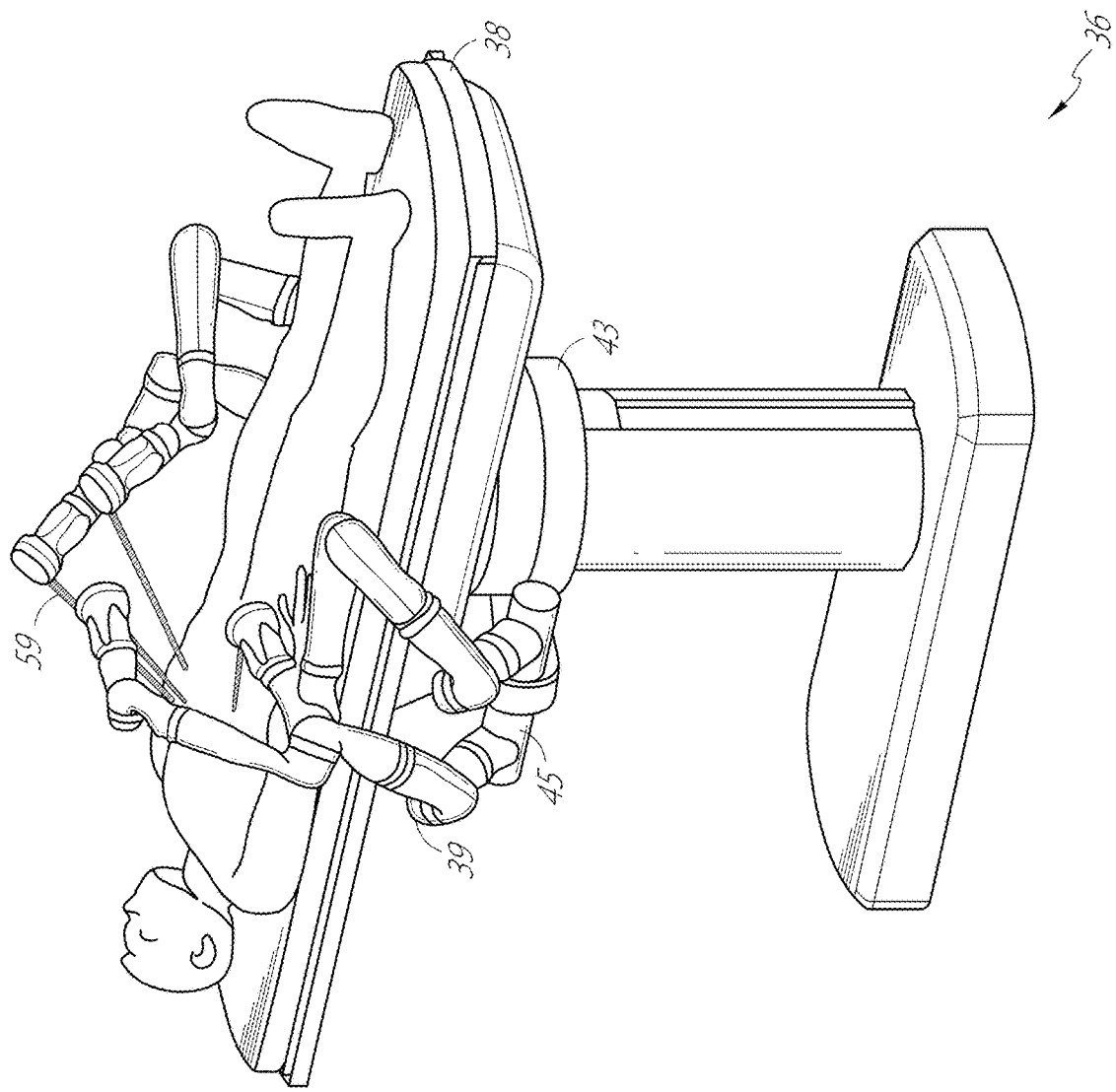
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based on the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
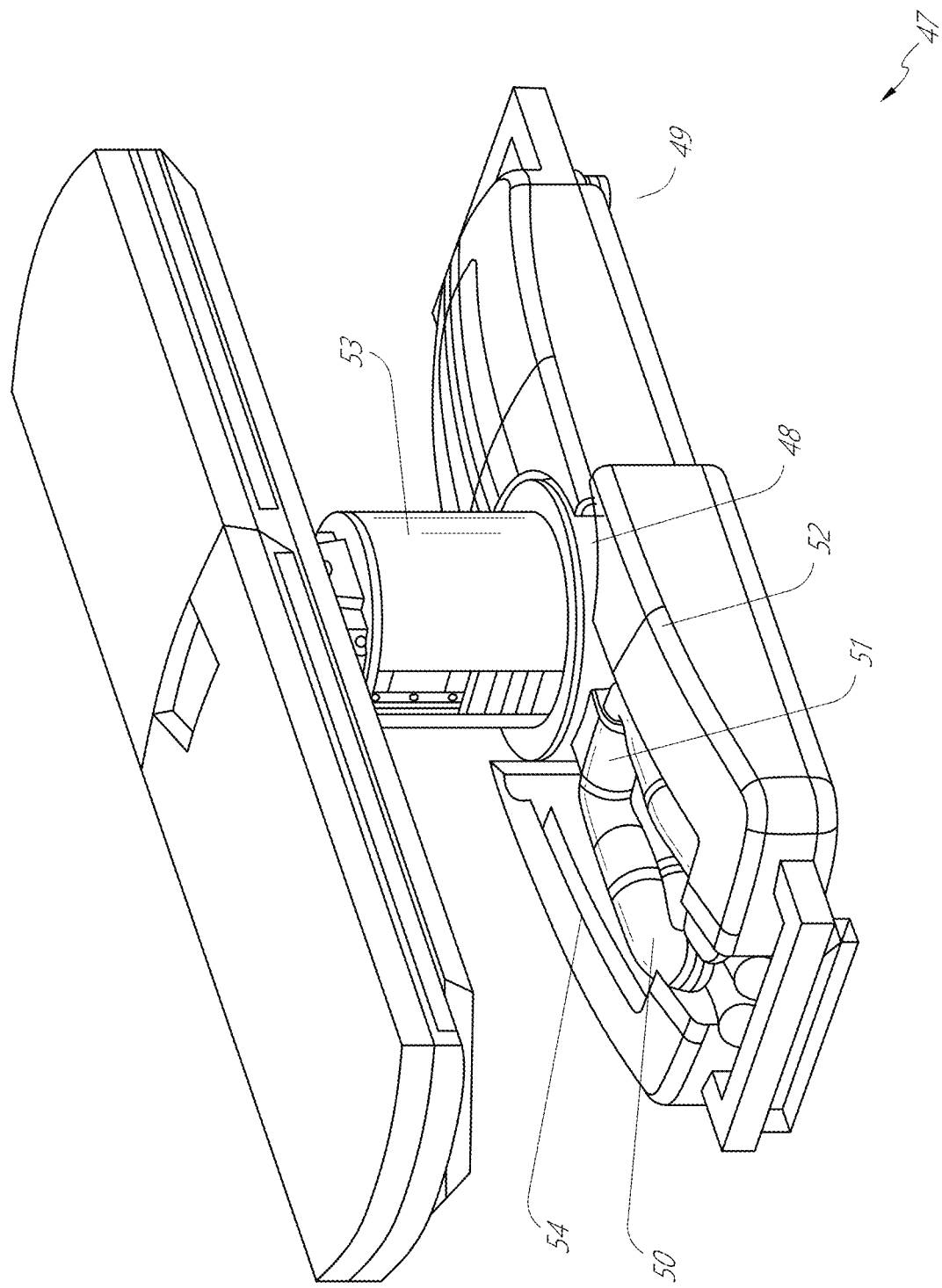
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
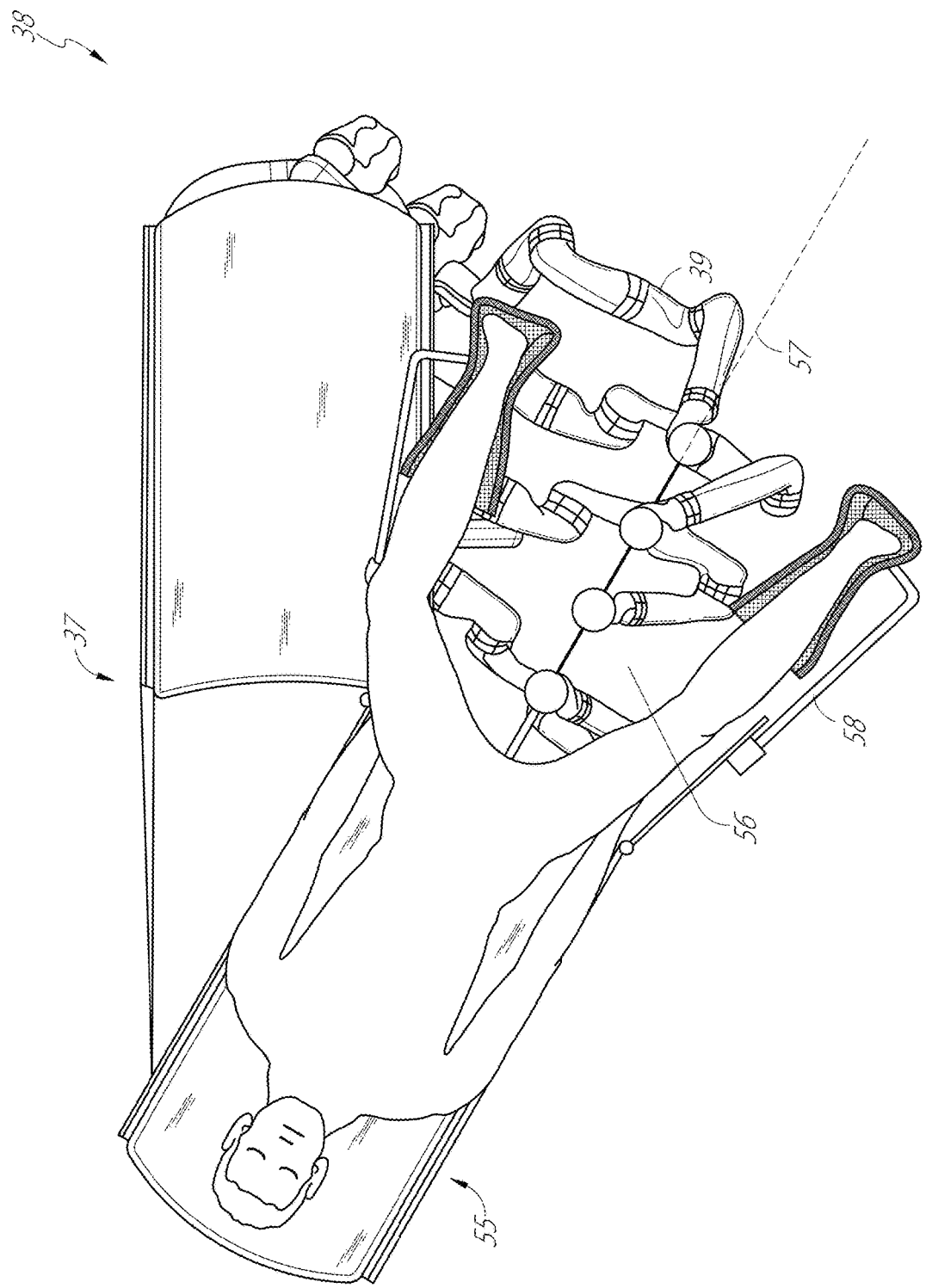
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
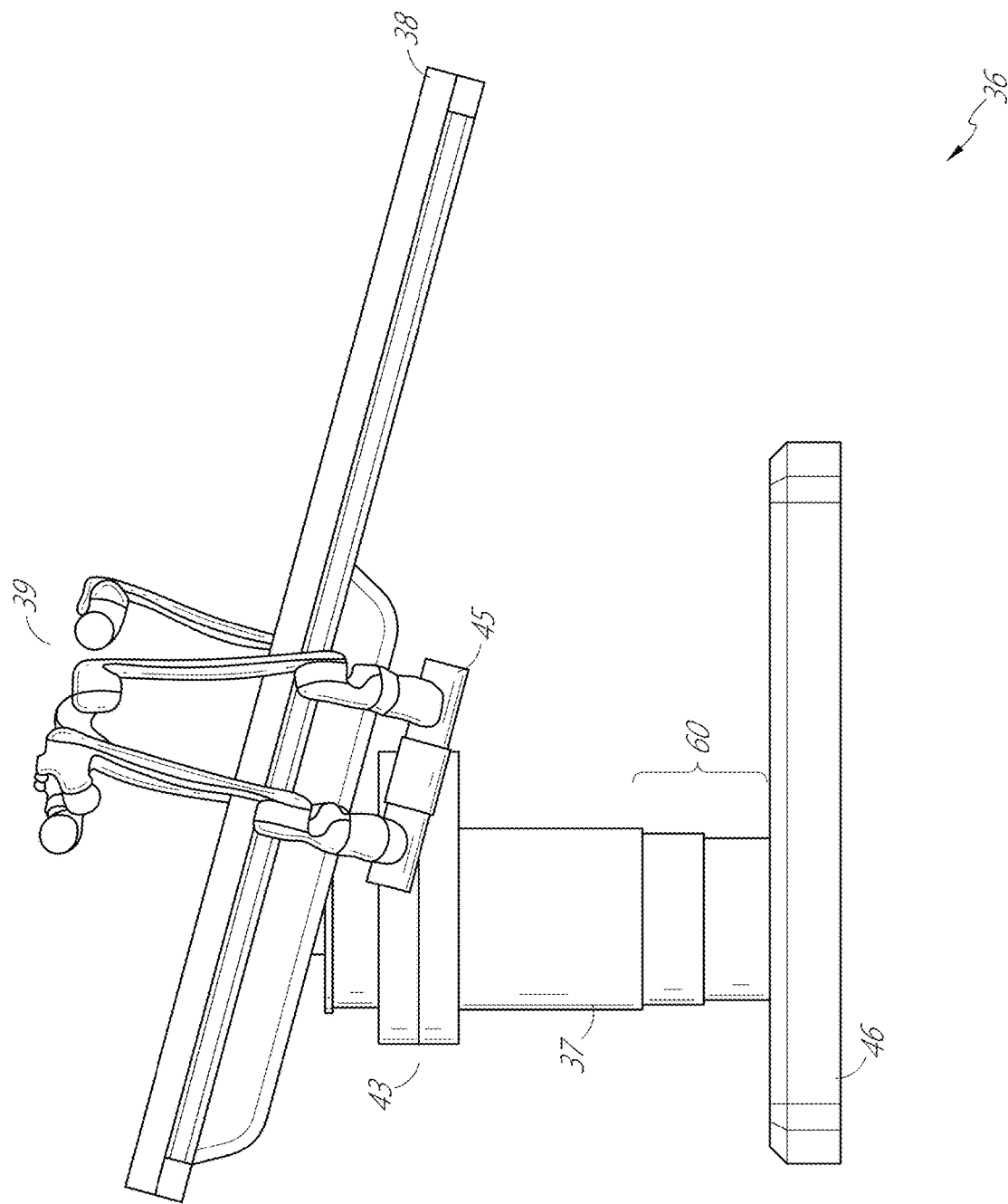
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
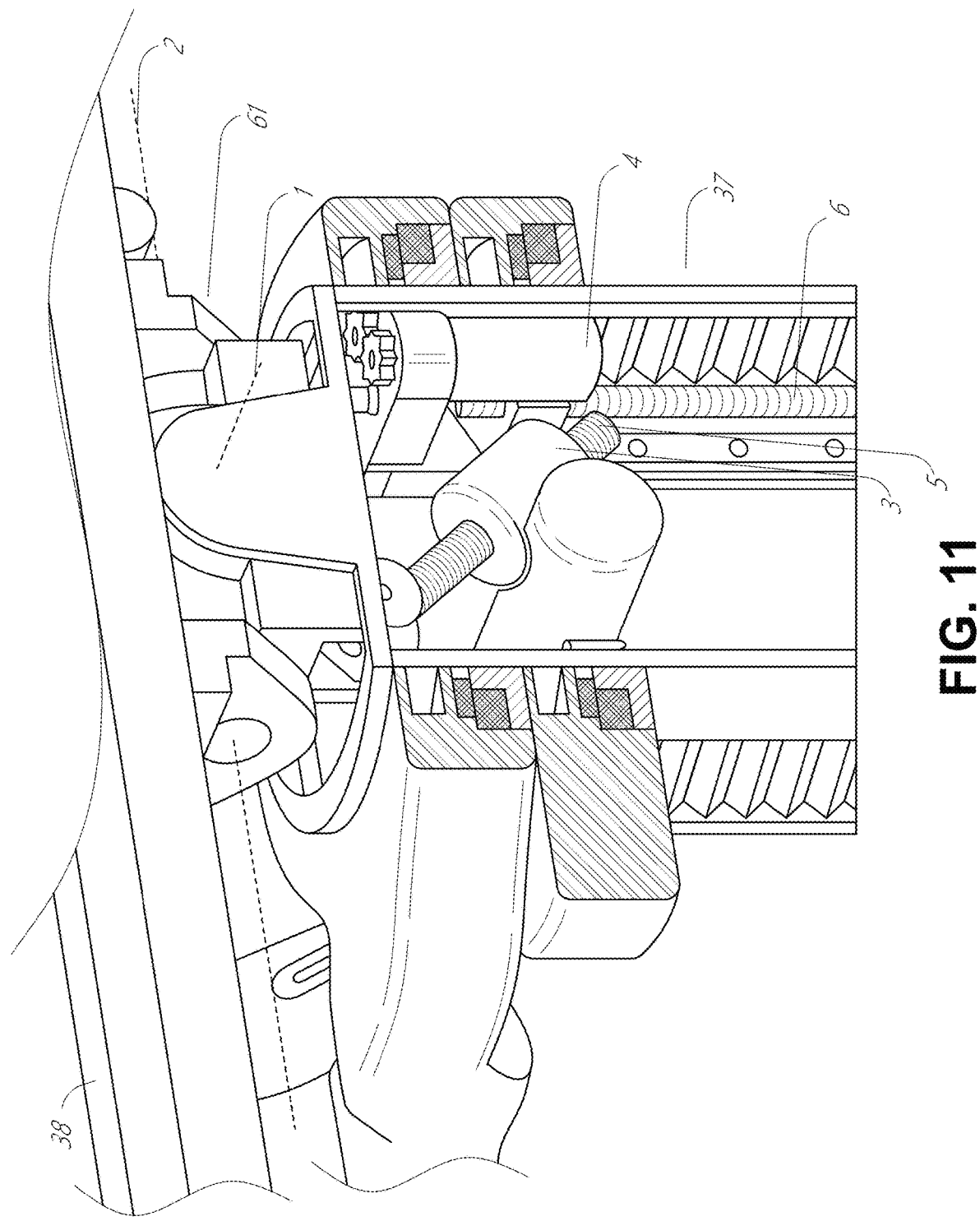
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
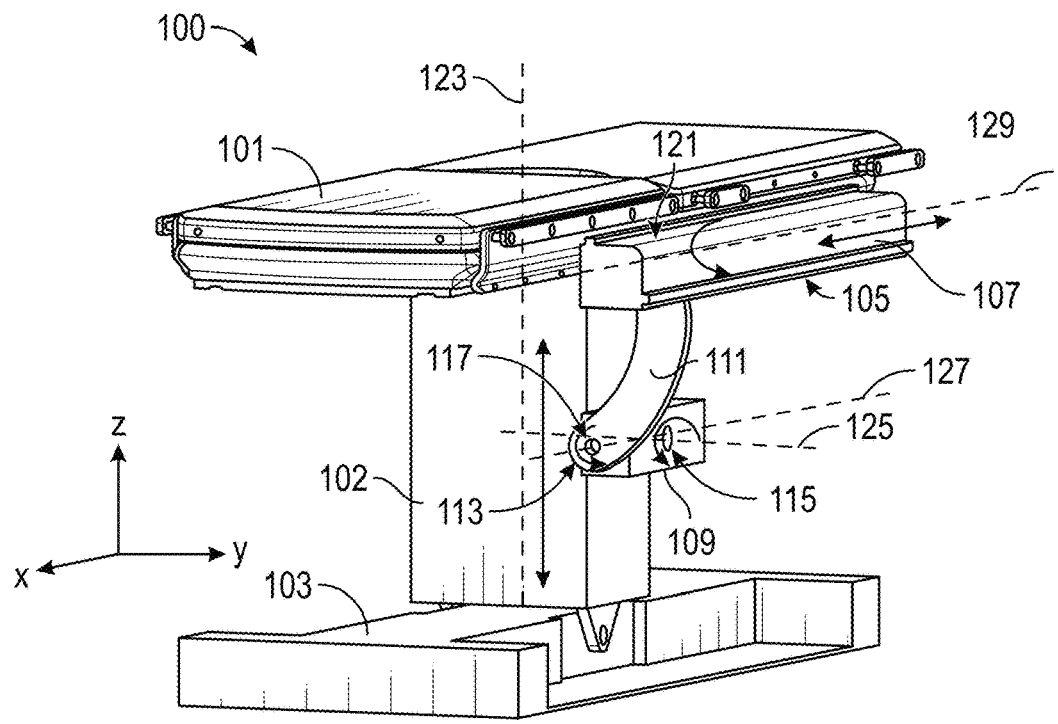
FIG. 12 illustrates an alternative embodiment of a table-based robotic system.
Figure 13:
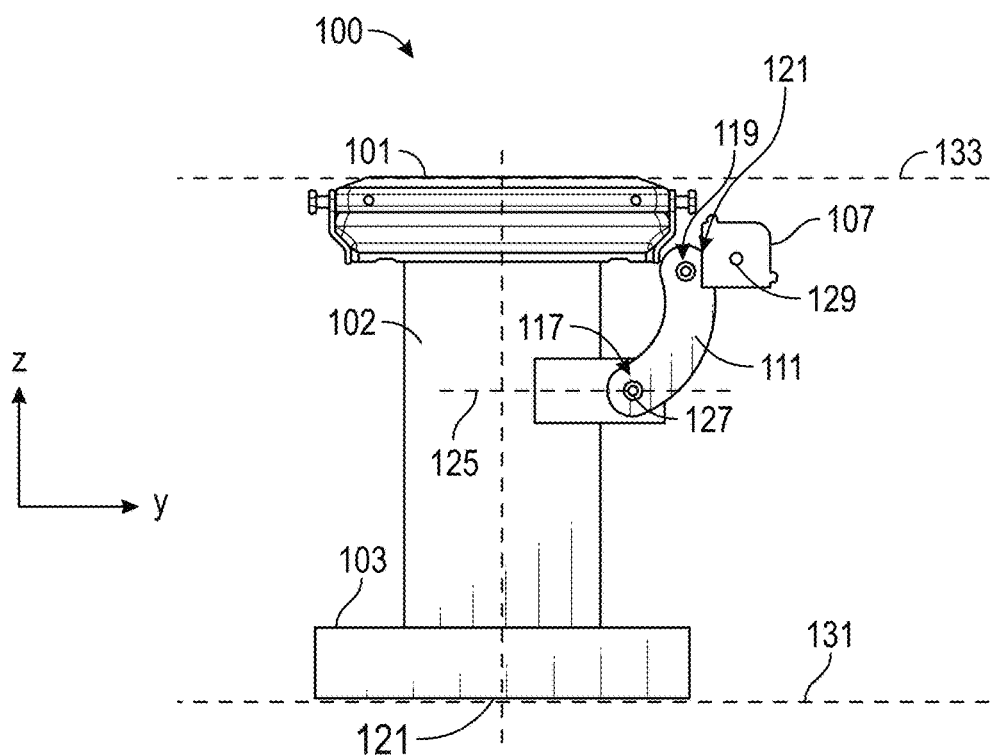
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom (Z-lift) to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
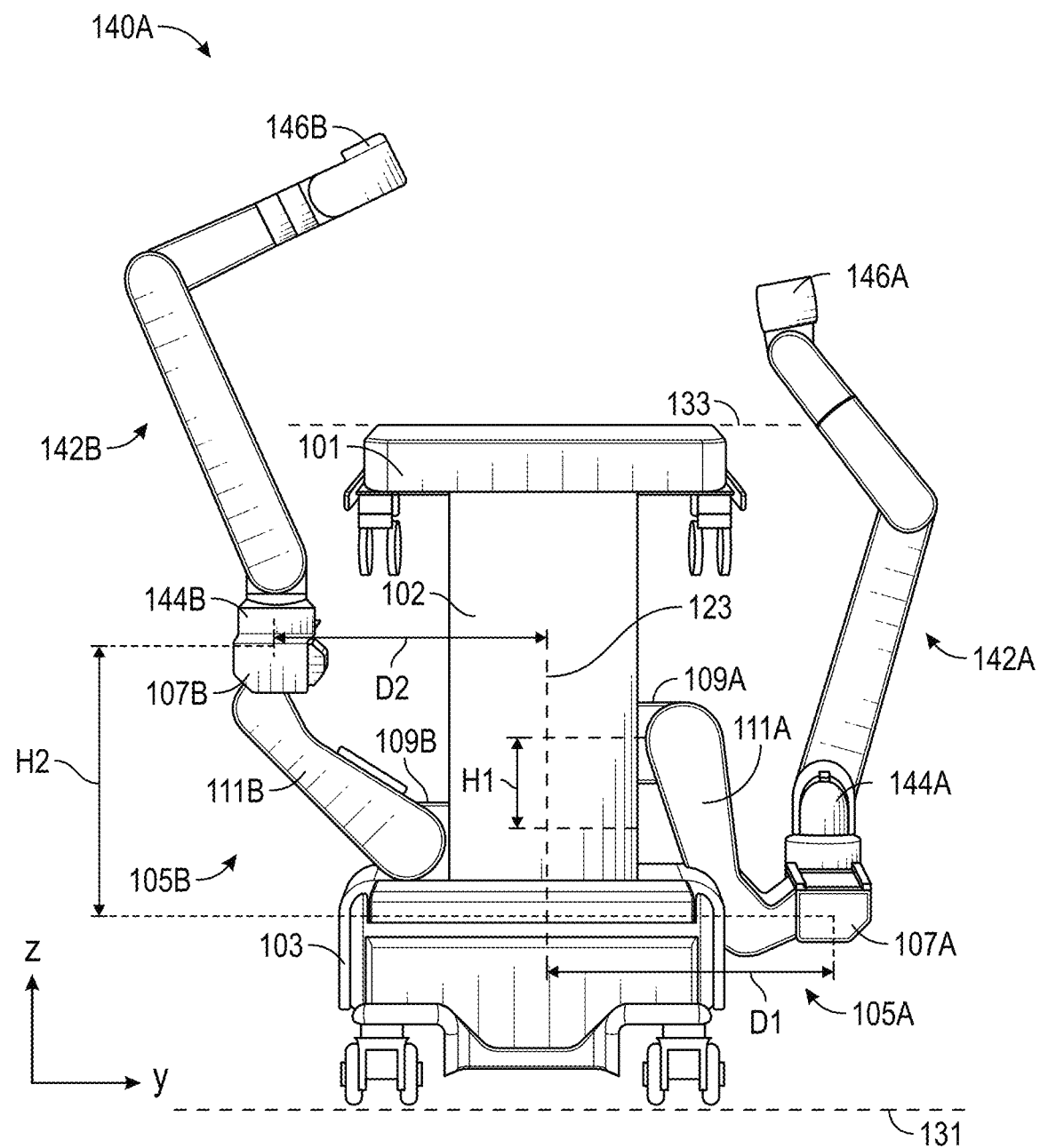
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
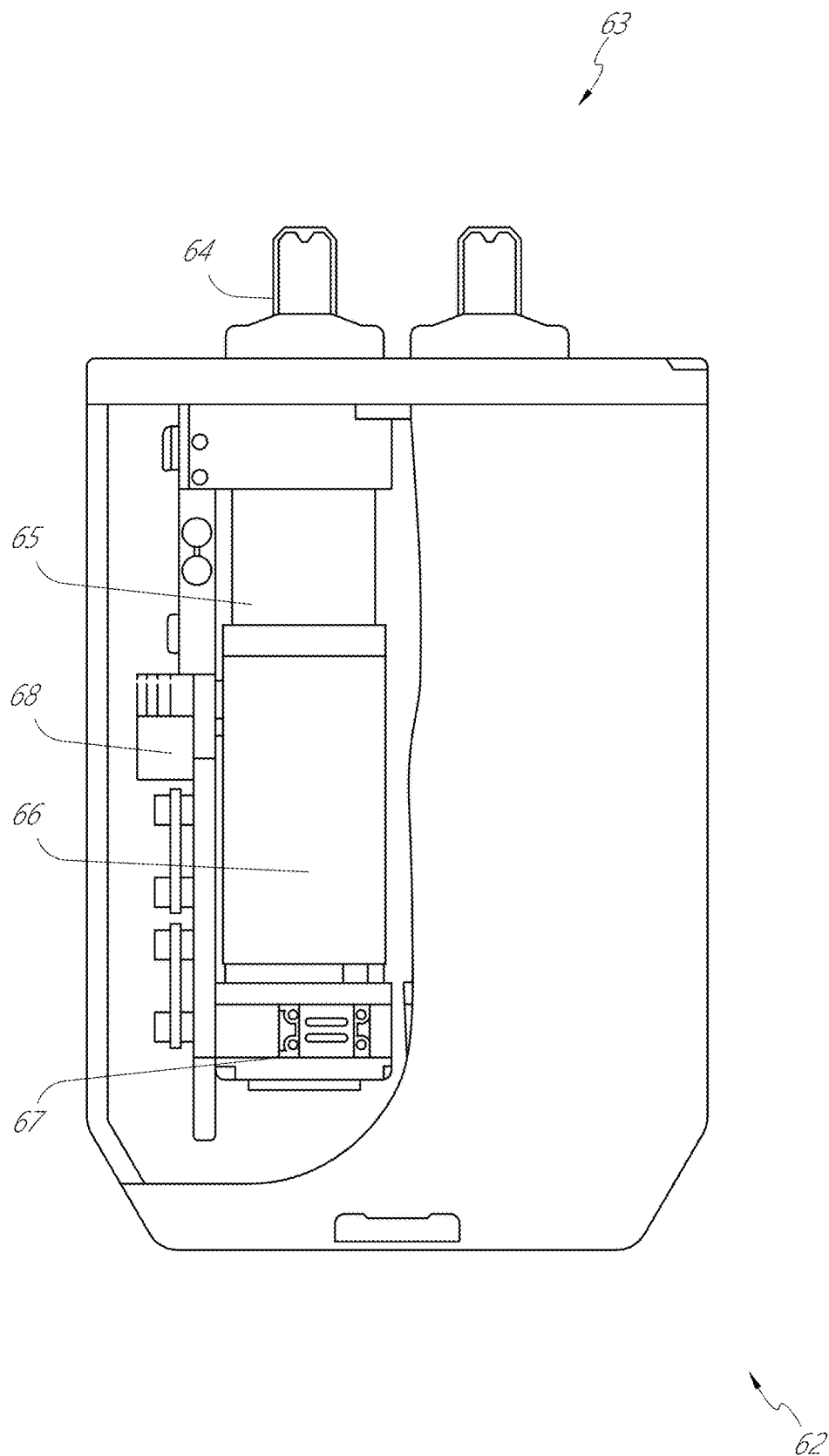
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
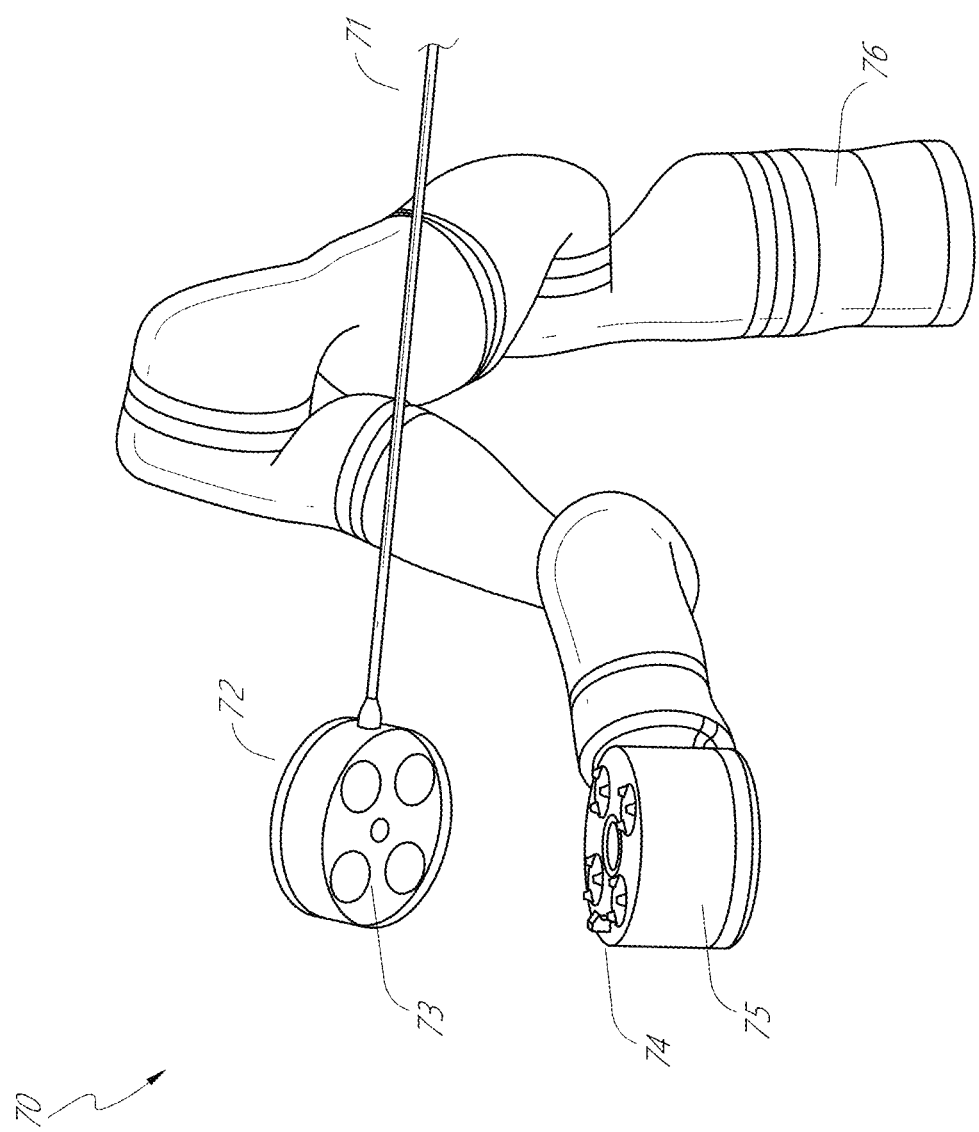
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
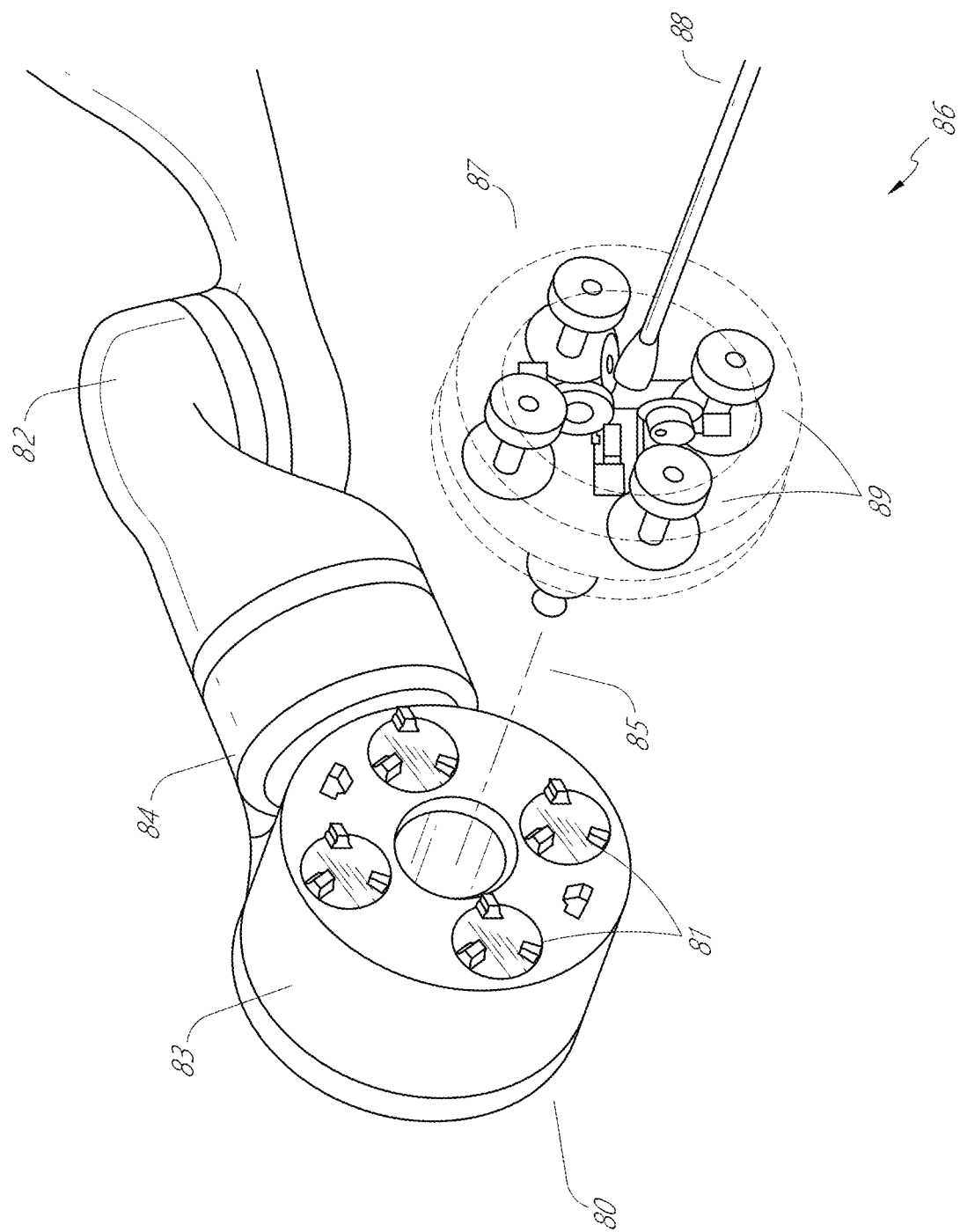
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
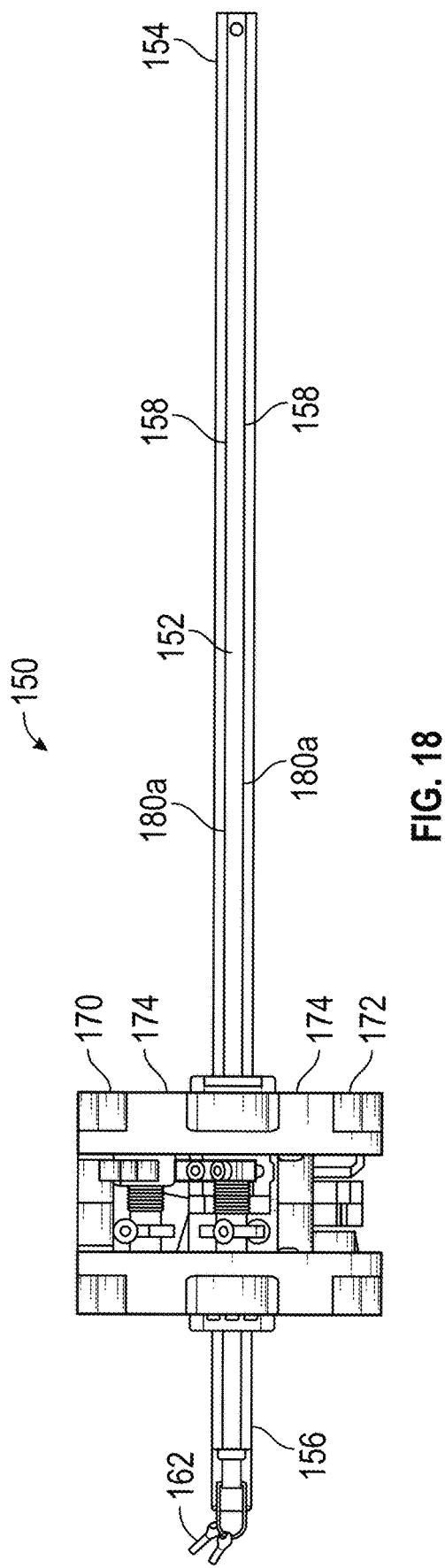
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
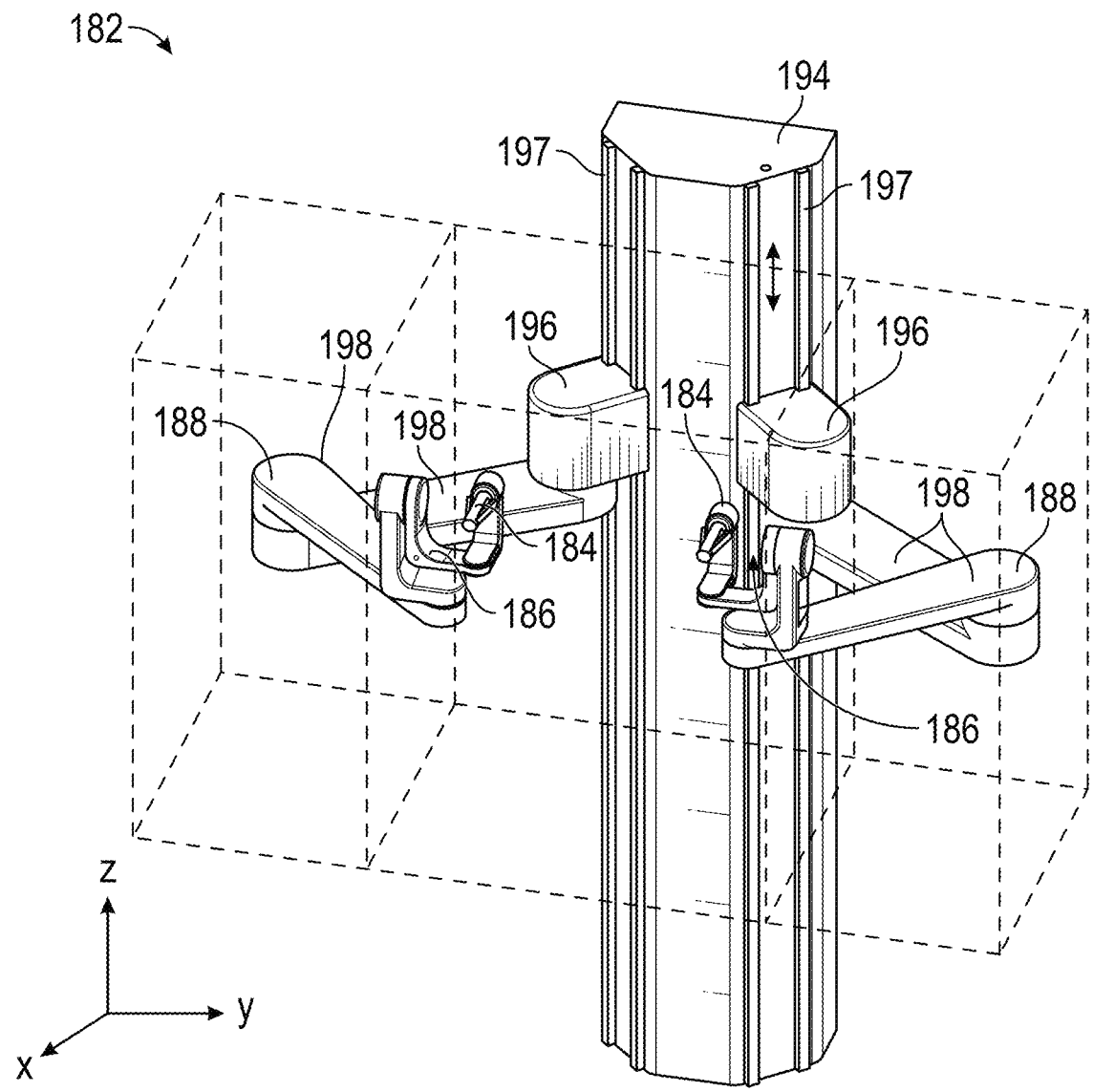
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
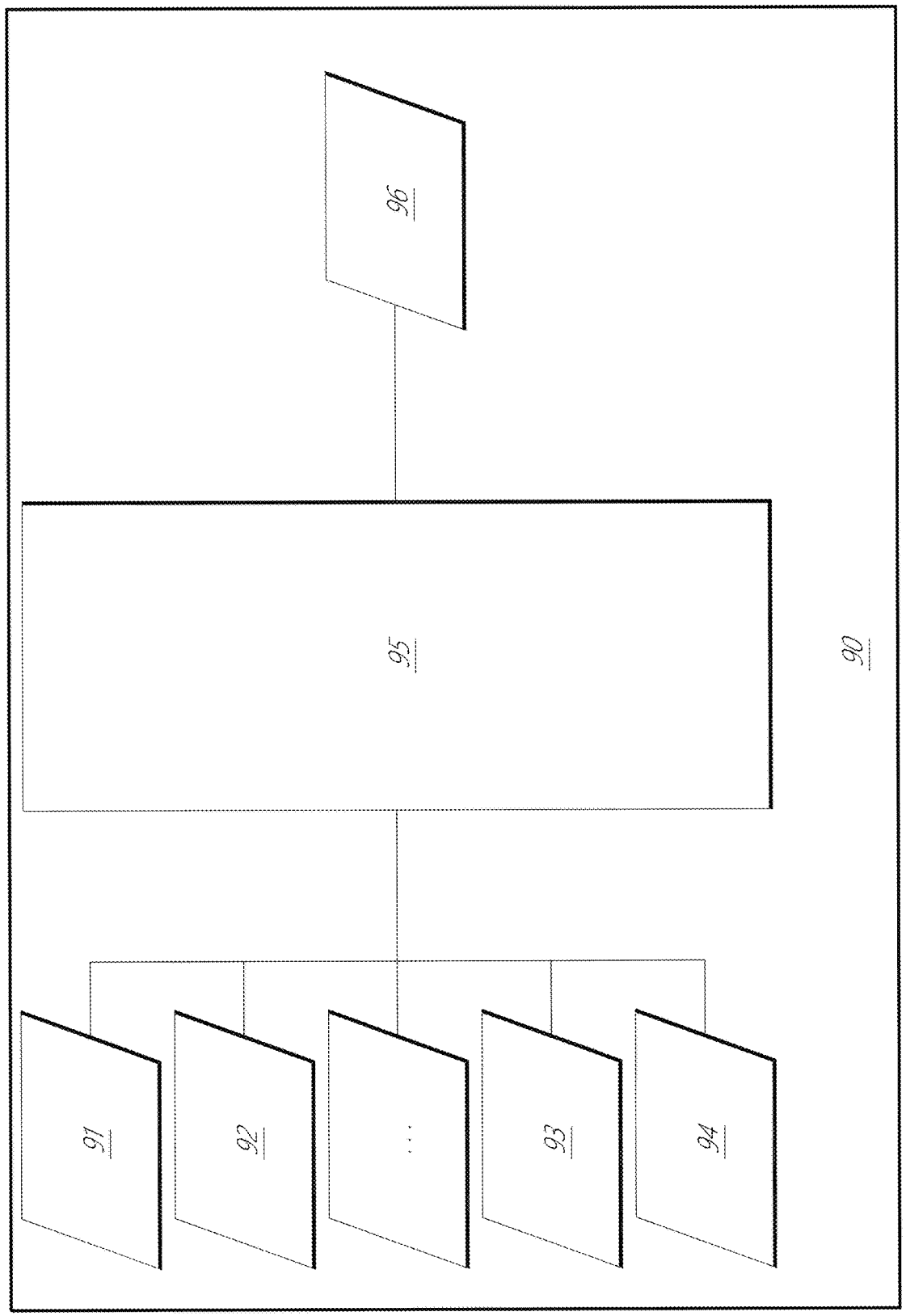
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Functional Indicators for Robotic Medical Systems.

Robotic medical systems can include indicators-such as visual or audible indicators, among others—that can be configured to communicate or otherwise provide information about the systems to users. Such indicators can be particularly useful for robotic medical systems that include a plurality of robotically controlled moveable components, although the indicators are also useful in less complex systems as well. The indicators can be configured to provide various functions as will be described below, including, for example, providing state and or identity information for the robotic system and/or components thereof. In some embodiments, state information can comprise, for example, a stand by state, a powered state, an active state, a ready state, an error state (e.g., a fault or collision state), a deployment state, a storage state, an emergency stop state, a motion (or impending motion) state, etc., of the robotic system and/or a component of the robotic system (such as a robotic arm, a medical instrument, an instrument driver, or an arm support). Identity information can comprise, for example, information that can be used to identify the robotic system and/or components thereof (for example, to distinguish one robotic arm from another or to distinguish one robotic tool from another).

As an initial example, the indicators can be configured to provide or communicate state and/or identity information about the system and/or its components. For example, an indicator can be configured to communicate that one or more components of the system are about to move and/or are moving. The indication can serve to notify users in the vicinity of the system about the movement so that unintentional contact between the users and the system can be avoided. Thus, in some embodiments, the indicators can be configured to provide information related to a movement state of the system. This can increase safety for those using this system.

As another example, an indicator can serve to provide identification information for a component of the robotic system. As noted above, a robotic system can include one or more robotic arms. An indicator can be configured to provide identification information associated with the one or more robotic arms. For example, a first robotic arm can be associated with an indicator of a first color, while a second robotic arm can be associated with an indicator of a second color. Users of the system can then identify the first and second robotic arms by referring to the first and second colors. This can facilitate use of the system by providing a mechanism by which the components of the robotic system can be identified and referenced. Advantageously, providing such identification information on the one or more robotic arms communicates to a clinician or clinician's assistant information with ease and enhances safety before and during a surgical procedure.

As will be described in more detail below, the indicators can advantageously be positioned on various components of the robotic system. In some embodiments, for example, the indicators can be positioned on adjustable arm supports and/or on a patient platform of the robotic medical system. Other locations for the indicators are also possible.

Figure 21A:
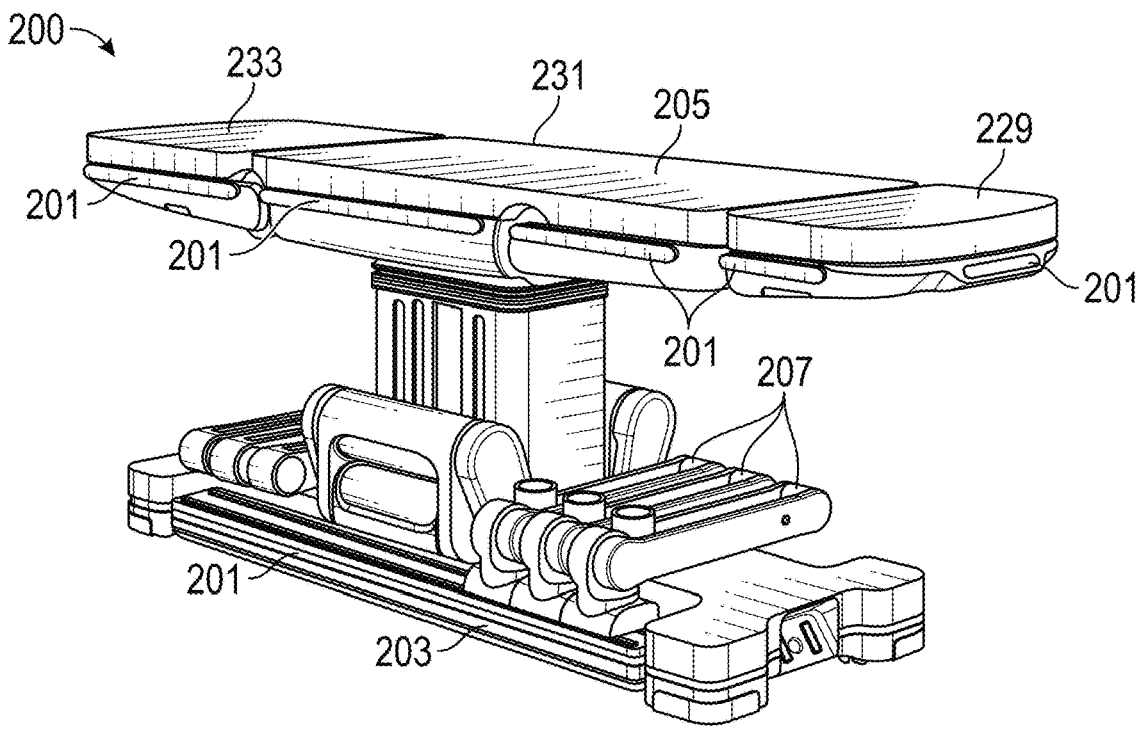
FIGS. 21A and 21B are perspective views of an embodiment of a robotic medical system including functional indicators.
Figure 21B:
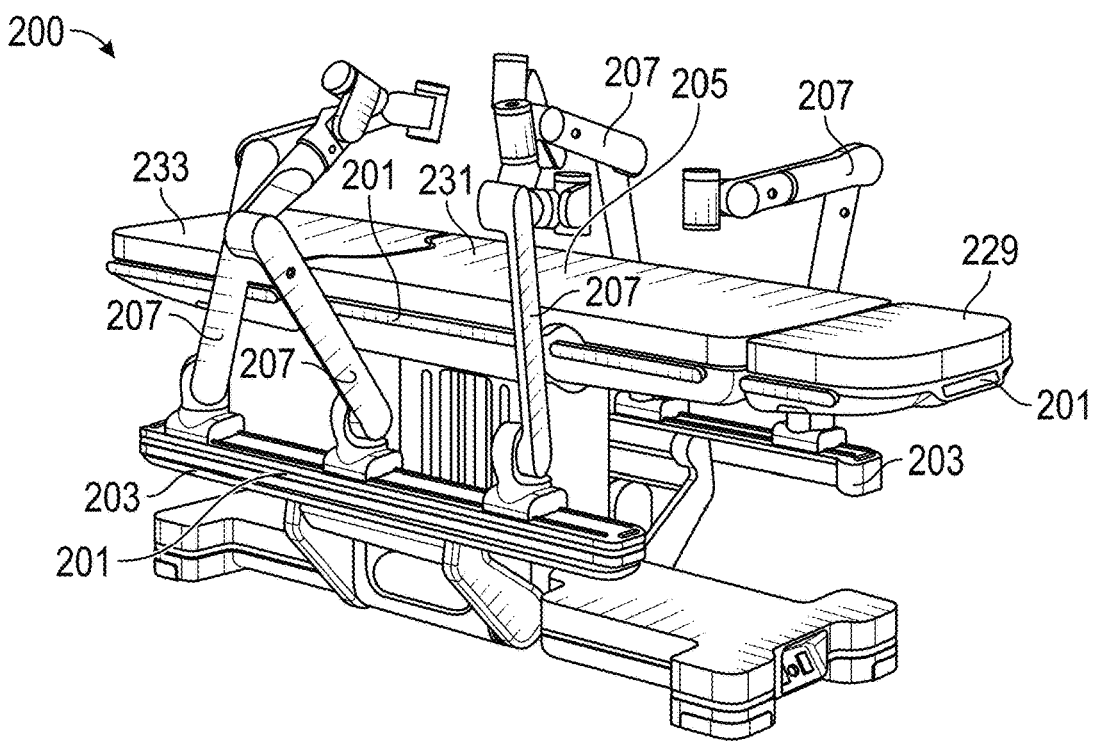

FIGS. 21A and 21B illustrate an embodiment of a robotic system 200 that may include one or more indicators 201. In the illustrated embodiment, the indicators 201 comprise light emitting diode (LED) light strips, although, as noted below, other types of indicators (e.g., other types of visual or audible indicators, etc.) can also be used. For example, other visual indicators can include lasers or moveable colored markers. Further, in the illustrated embodiment, the indicators 201 are positioned on adjustable arm supports 203 and a patient platform 205 of the system 200. The illustrated positions of the indicators 201 are provided by way of example, not limitation. Further, not all indicators 201 need be included in all embodiments. For example, in some embodiments, the indicators 201 can be omitted from the patient platform 205 or the adjustable arm supports 203.

The system 200 can be similar in some respects to the systems 100, 140A described above with reference to FIGS. 12-14. For example, the adjustable arm supports 203 can be similar to the adjustable arm supports 105, and the patient platform 205 can be similar to the patient platform 101 previously described. The patient platform 205 is configured to support a patient during a robotic medical procedure. The adjustable arm supports 203 can be configured so as to be moveable or adjustable relative to the patient platform 205, in a similar manner as described above with reference to the systems of FIGS. 12-14.

In the illustrated embodiment, the adjustable arm supports 203 include a rail or bar that can be configured to support one or more robotic arms 207. The adjustable arm supports 203 and robotic arms 207 can be moved between a wide variety of positions, for example, to facilitate a robotic medical procedure (e.g., to a position as shown in FIG. 21B) and/or to facilitate storage of the adjustable arm supports 203 and robotic arms 207 beneath the patient platform 205 (e.g., as shown in FIG. 21A). As described above with reference to FIGS. 12-14, the adjustable arm supports 203 can be configured for movement in multiple degrees of freedom. For example, the adjustable arm supports 203 can move in all three spatial directions, including up and down, and enable the robotic arms 207 that are attached thereto to be stored underneath the patient platform 205.

As apparent from the preceding description, the robotic medical systems 200 can include a plurality of moveable/adjustable robotic components. In view of the high degree of movement, it can become important that the system 200 is configured to effectively and efficiently communicate various types of information about the system to users. As described below, the indicators 201 described in this section can be configured for this and other purposes. For example, during movement of components of the system 200, there can be a risk of harm to users of the systems in a variety of situations. One such situation is the deployment of the robotic arms 207 as they are moved from their stowed position under the patient platform 205 to a deployed position on either side of the patient platform 205. Another potentially dangerous situation is the autonomous or remotely controlled movement of the arm supports 203 during a procedure, whereby the risk can be particularly pronounced for any sterile users supporting the procedure that are, for example, standing next to the system. As described in more detail below, the indicators 201 described herein can be configured to communicate information regarding movement or other states of the various robotic components of the system to nearby users to mitigate the risk of harm or otherwise facilitate a robotic medical procedure. As one example, an indicator 201 can flash or change color to indicate that an associated robotic component is about to move. This may provide an indication to users in the vicinity to keep clear, improving safety in the operating room.

These and other features and functions of the indicators 201 and system 200 will become more fully apparent from the following sections that describe (A) indicators 201 on arm supports 203, (B) indicators 201 on patient platforms 205, and (C) functions or features that can be provided by the indicators 201. Although sections (A) and (B) describe example indicator locations on arm supports 203 and patient platforms 205, other locations for indicators 201 are also possible. Further, the indicators 201 can also be used in other types of medical systems that may not include adjustable arm supports 203 or patient platforms 205.

A. Indicators on Arm Supports.

As shown in FIGS. 21A and 21B, in some embodiments, indicators 201 can be included on each of the adjustable arm supports 203 of the system 200. This may be advantageous because it can provide indicators on each side of the patient platform 205 (if adjustable arm supports 203 are included on each side as illustrated) and can provide the indicators directly on one of the moveable components of the system 200. In the illustrated embodiment, the indicators 201 on the adjustable arm supports 203 comprise one or more lights (e.g., LEDs or LED arrays), while in other embodiments, the indicator/signifier can comprise one or more audible speakers (see FIG. 26) or a combination of a visual and audible indicators (e.g., LEDs embedded in the speakers themselves). The indicators 201 can be used at different periods of a surgical procedure, including during set-up, intraprocedure, or take-down.

In the illustrated embodiment of FIGS. 21A and 21B, the indicator 201 on the adjustable arm support 203 comprises an LED light strip that is positioned along one or more side surfaces of the adjustable arm support 203. In some embodiments, one or more additional indicators 201 can also be provided, alternatively or additionally, on one or more additional surfaces of the adjustable arm support 203 as shown, for example, in FIGS. 22A-22D. FIGS. 22A-22D illustrate example indicators 201 on the adjustable arm support 203 (e.g., on the bar or rail of the adjustable arm support 203) according to several embodiments to illustrate certain features of this disclosure.

Figure 22A:
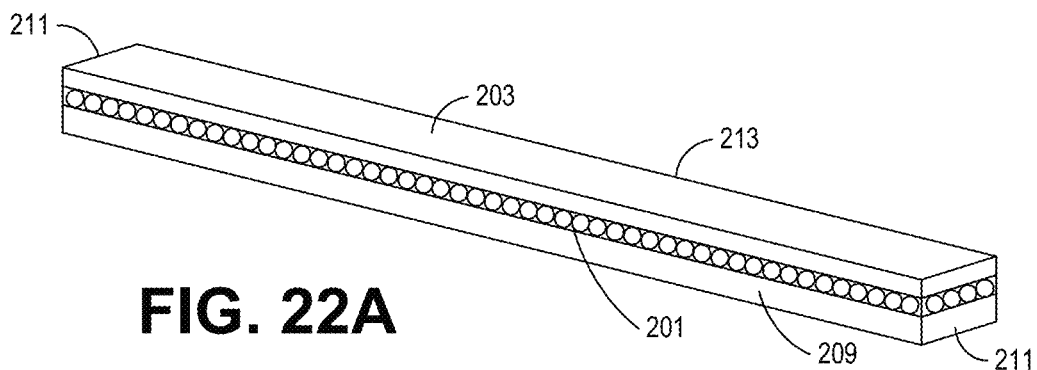
FIG. 22A illustrates an embodiment an adjustable arm support including a functional indicator comprising an light emitting diode (LED) strip.

FIG. 22A is a perspective view of an adjustable arm support 203 that includes an indicator 201. In the illustrated embodiment, the indicator 201 comprises an LED light strip. The LED light strip can include a plurality of LEDs. The LEDs can be individually addressable such that they can be controlled individually. Thus, in some embodiments, different portions or regions of the indicator 201 can be activated (e.g., lit up) or deactivated (e.g., turned on) individually as will be described in more detail below. Further, in some embodiments, the LEDs of the indicator 201 may be configured to light up in different colors and/or to provide illumination at different intensities. Although described as including LEDs, other types of light-based indicators can also be used. In addition, though not shown in FIG. 22A, speakers and/or other indicators/signifiers may be included with the LEDs.

In the illustrated embodiment, the indicator 201 is positioned on an outer surface 209 of the adjustable arm support 203. The outer surface 209 may be a surface of the adjustable arm support 203 that faces away from the patient platform 205. This placement location can provide good visibility to users standing on the side of the patient platform 205. Additionally, in the illustrated embodiment of FIG. 22A, the indicator 201 extends onto end surfaces 211 of the adjustable arm support 203. Thus, the indicator 201 can "wrap around" the adjustable arm support 203. In some embodiments, the indicator 201 extends onto both end surfaces 211 of the adjustable arm support. In some embodiments, indicators 201 that wraparound multiple surfaces of the adjustable arm support 203 can be visible to users positioned at different locations around the patient platform 205, such as at the head end or foot end of the patient platform 205. Although not visible in FIG. 22A, in some embodiments, the indicator 201 can further extend onto an inner surface 213, upper surface, and/or lower surface of the adjustable arm support 203. Also, although the indicator 201 is illustrated as a continuous strip in FIG. 22A, this need not be the case in all embodiments, as shown, for example, in the embodiment of FIG. 22B.

Figure 22B:
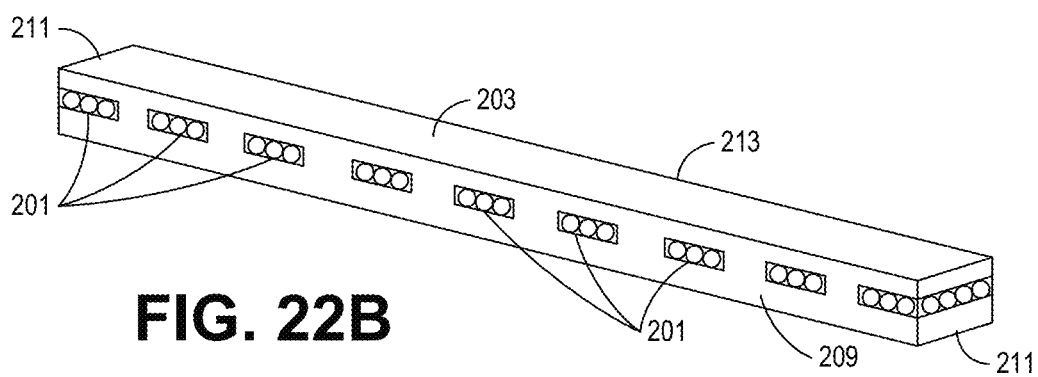
FIG. 22B illustrates an embodiment of an adjustable arm support including a functional indicator comprising a plurality of discrete LEDs or discrete LED strips.

FIG. 22B illustrates a perspective view of an additional embodiment of an adjustable arm support 203 that includes a plurality of discrete indicators 201. In the illustrated embodiment, the indicators 201 are illustrated as light sources, such as LEDs, although other types of indicators 201 can be used. The individual or discrete indicators 201 can be individually addressable such that they can be controlled individually. Thus, in some embodiments, different indicators 201 can be activated (e.g., lit up) or deactivated (e.g., turned on) individually as will be described in more detail below. Further, in some embodiments, the LEDs of each indicator 201 may be configured to light up in different colors. In the illustrated embodiment, the individual indicators 201 are positioned on the outer surface 209 of the adjustable arm support 203. Additionally, indicators 201 are positioned so as to extend onto the end surfaces 211 of the adjustable arm support 203.

Figure 22C:
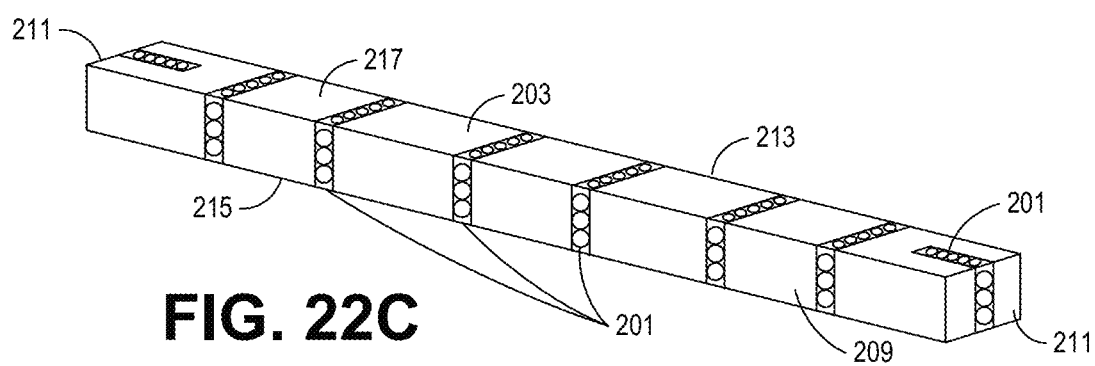
FIG. 22C illustrates another embodiment of an adjustable arm support including a functional indicator comprising a plurality of discrete LEDs or discrete LED strips.

FIG. 22C illustrates an additional embodiment of an adjustable arm support 203 that includes a plurality of discrete indicators 201. In this embodiment, the indicators 201 comprise light strips (e.g., LED strips) that wrap around a lower surface 215, the outer surface 209, and an upper surface 217 of the adjustable arm support 203. In some embodiments, the indicators 201 may further extend onto the inner surface 213 of the adjustable arm support 203. As noted before, the indicators 201 can be individually addressable and controllable and/or configured to provide light of different colors and/or intensities.

Figure 22D:
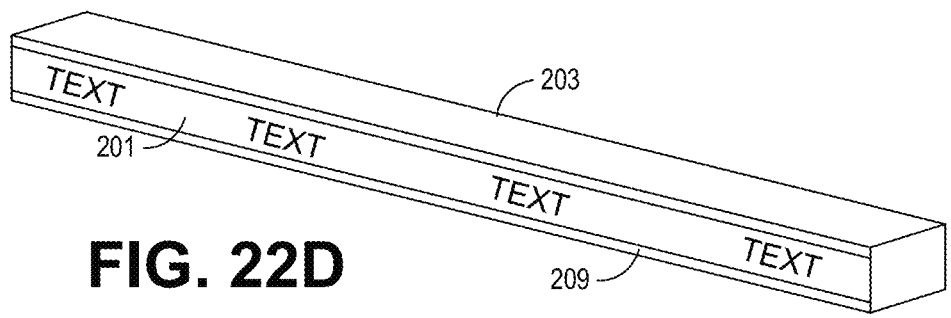
FIG. 22D illustrates an embodiment of an adjustable arm support including a functional indicator configured as a screen.

FIG. 22D illustrates an additional embodiment of an adjustable arm support 203 that includes an indicator 201 that is configured to display text, symbols, images, etc. For example, the indicator 201 can comprise a matrix of individually addressable light sources (e.g., LEDs) or any other type of screen (e.g., an LCD, an LED, or an OLED screen). Such an indicator 201 may be capable of providing more complex information, such as text or diagrams, to a user. In the illustrated embodiment, the indicator 201 is positioned on the outer surface 209 of the adjustable arm support 203. Other locations for the indicator 201 are also possible (such as any of the other surfaces) and can be used in place of or in addition to the indicator 201 as illustrated.

Figure 23A:
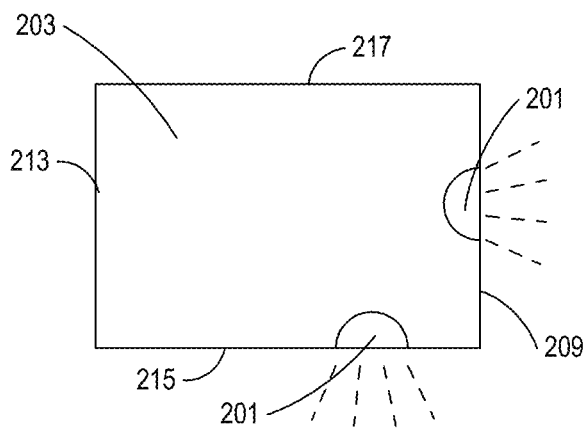
FIG. 23A illustrates a cross-sectional view of an embodiment of an adjustable arm support including functional indicators on outer and lower surfaces thereof.
Figure 23B:
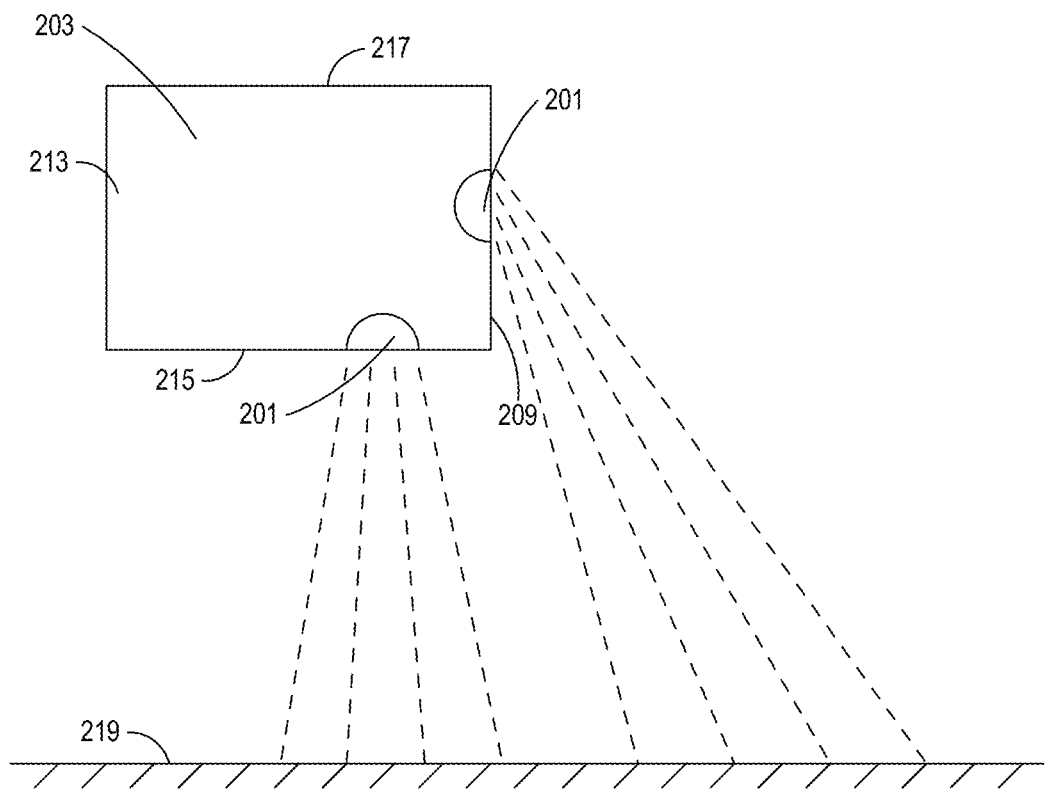
FIG. 23B illustrates a cross-sectional view of another embodiment of an adjustable arm support including functional indicators on outer and lower surfaces thereof.

FIGS. 23A and 23B illustrate cross-sectional views of an adjustable arm support 203 including one or more indicators 201, in accordance with some embodiments. In the illustrated embodiment, the adjustable arm support 203 includes indicators 201 positioned on an outer surface 209 and a lower surface 215 thereof. Further, in the illustrated embodiment, the indicators 201 comprise light sources, such as LEDs. FIGS. 23A and 23B illustrate that the indicators 201 can be configured to provide different types of illumination, among other functions. For example, in FIG. 23A, the indicators 201 are configured to provide generally diffuse light that is emitted from the indicator 201 in numerous general directions. FIG. 23B, on the other hand, illustrates that the indicators 201 can be configured to provide light that is focused in a particular direction. For example, as shown in FIG. 23B, both the indicator 201 positioned on the lower surface 215 and the indicator 201 positioned on the outer surface 209 are configured to provide light that is focused towards the ground 219. As will be described in more detail below with reference to FIGS. 27A and 27B, light which illuminates the ground can be used for general illumination and/or to identify one or more zones around a robotic medical system. In some embodiments, light which is illuminated downward, whether directed specifically downward or not, may be beneficial as it may be more easily seen when components of the robotic system are covered by a sterile drape.

Figure 24:
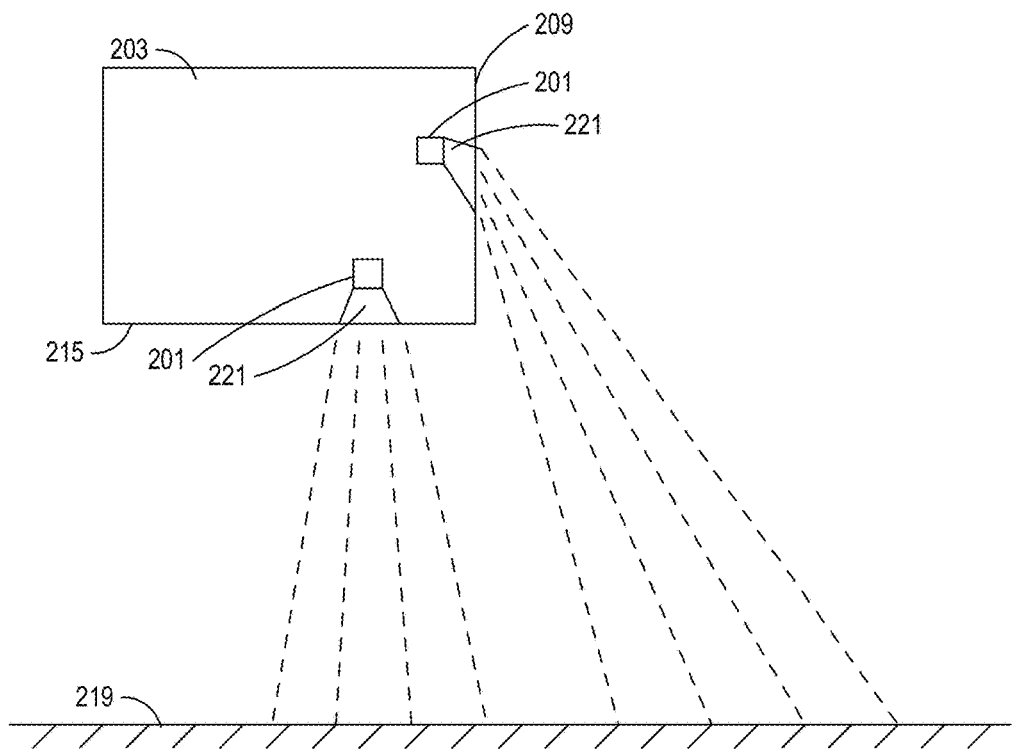
FIG. 24 illustrates a cross-sectional view of an adjustable arm support including functional indicators comprising light guides.

FIG. 24 illustrates a cross-sectional view of an adjustable arm support 203 including indicators 201 that are embedded within the adjustable arm support 203, in accordance with some embodiments. In the illustrated embodiment, the indicators 201 comprise light sources, such as LEDs. The light from the indicators 201 can be directed in desired directions using light guides 221. As shown in the illustrated embodiment of FIG. 24, the light guides 221 can be configured to direct light emitted from the indicators 201 towards the ground 219. This, however, need not always be the case, and the light guides 221 can be configured to orient the light from the indicators in other directions.

Figure 25:
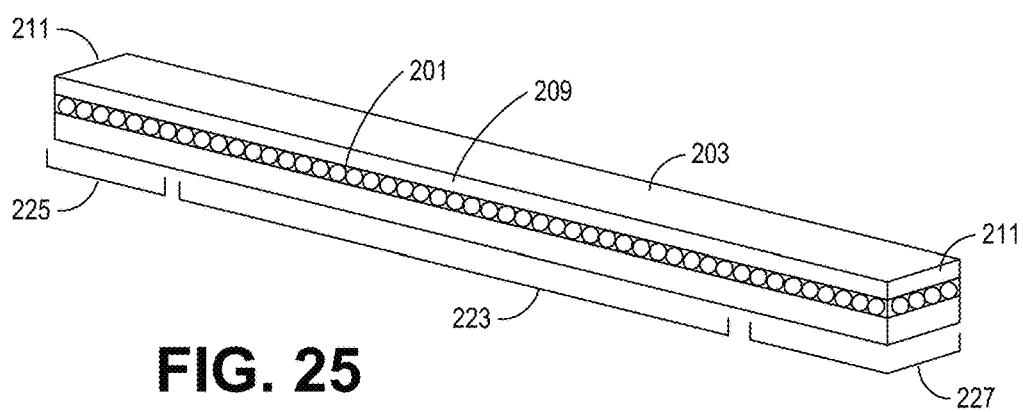
FIG. 25 illustrates an embodiment of an adjustable arm support including a plurality of different indicator zones.

As mentioned above, the indicator(s) 201 can be configured with different segments or zones that can be individually controlled. FIG. 25 illustrates an example adjustable arm support 203 that includes an indicator 201 that comprises a plurality of individual zones 223, 225, 227. In the illustrated embodiment, the indicator 201 comprises an LED light strip as described above with reference to FIG. 22A. In the embodiment of FIG. 25, a center zone 223 and two end zones 225, 227 can each be independently controllable such that they can be activated or deactivated individually. As will be described below, activating different zones of the indicator 201 can be useful for indicating different states or identity information for a robotic system. Although FIG. 25 illustrates three zones, other numbers of individually controllable zones are also possible. For example, the indicator 201 can comprise one, two, three, four, five, six, seven, eight, nine, ten, or more zones. As mentioned above, in some embodiments, each light of the indicator 201 can be individually controllable.

Figure 26:
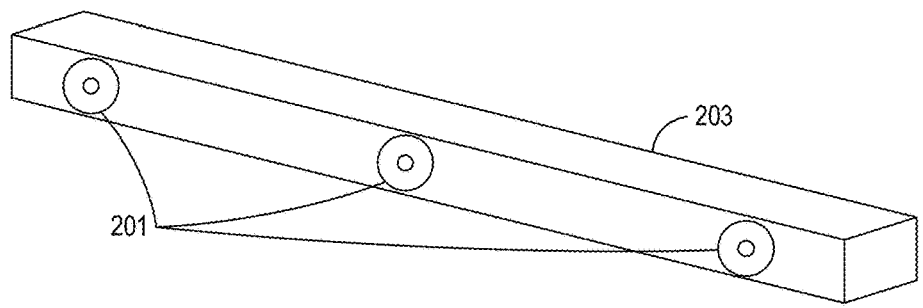
FIG. 26 illustrates an embodiment of an adjustable arm support including indicators configured as audio devices.

In each of the embodiments of FIGS. 22A-25 described above, the indicators 201 comprise light sources. Other types of indicators (such as audible indicators, for example) can also be used, in addition to or in place of the visual or light-based indicators 201. FIG. 26, for example, illustrates an embodiment where the indicators 201 comprises audio devices, such as speakers, configured to provide audible alerts or indications. In the illustrated embodiment, three speaker-type indicators 201 are illustrated on an outer face of the adjustable arm support 203. Other numbers and placements for audible indicators 201 can be included in other embodiments.

FIGS. 22A-26 are intended to provide examples of placement locations for indicators 201 on adjustable arm supports 203. The illustrated embodiments are not intended to be limiting and other locations and placements for the indicators 201 on the adjustable arm supports 203 are also possible. In the alternative, or in addition, other types of combinations indicators 201 may be placed on one or more of the arm supports 203. In addition, the indicators in FIGS. 22A-26 may not be exclusive from one another. For example, in some embodiments, the light strip in FIG. 22A can be combined with indicators on a lower surface of the arm support as shown in FIG. 23A.

B. Indicators on Patient Platforms.

As shown in FIGS. 21A and 21B, indicators 201 can be positioned on the patient platform 205. The indicators 201 on the patient platform 205 can be included in addition to or in place of the indicators 201 on the adjustable arm supports 203 described previously. In some embodiments, the indicators 201 on the patient platform 205 can share the same or similar functions as the indicators 201 on the adjustable arm supports 203, as described above. In some embodiments, the patient platform 205 is adjustable, such that an angle of the patient platform 205 can be adjusted as desired. For example, the patient platform 205 can be configured to allow for longitudinal and/or lateral tilt. In some embodiments, tilt of the patient platform 205 can be robotically controlled.

In the illustrated embodiment, the patient platform 205 includes a head section 229, a torso section 231, and a leg section 233. The head section 229 can be configured to support a head of a patient, the torso section 231 can be configured to support a torso of the patient, and the leg section 233 can be configured to support legs of the patient. In some embodiments, one or more of these sections 229, 231, 233 is configured to be independently adjustable. For example, in some embodiments, an angle or pitch of one or more of these sections 229, 231, 233 is configured to be independently adjustable. Adjustment of the sections 229, 231, 233 may allow the patient platform 205 to position the patient in various orientations that can be advantageous for a medical procedure.

As illustrated, the patient platform 205 can include one or more indicators 201. The indicators 201 on the patient platform 205 may be any type of indicator as described above, including visual and audible indicators. In the illustrated embodiment, the indicators 201 comprise visual indicators configured as LED strips. As shown in the illustrated embodiment, discrete LED strips can be arranged along one or more of the edges or sides of the head section 229, the torso section 231, and the leg section 233. For example, in the illustrated embodiment, indicators 201 are positioned on lateral sides of each of the head section 229, the torso section 231, and the leg section 233. In some embodiments, the indicators 201 are included only on some of the sections 229, 231, 233. For example, the indicators 201 may be positioned only on the torso section 231.

Further, in the illustrated embodiment, indicators are also positioned on ends of the patient platform 205. As shown in FIGS. 21A and 21B, an indicator 201 is included on the end of the head section 229. An indicator 201 can also be included on an end of the leg section 233.

Positioning the indicators 201 on more than one side of the patient platform 205 can increase the likelihood that users located at different positions around the table can see the indicators 201. When positioned on multiple sides of the patient platform 205, the indicators 201 can be considered to "wrap around" the patient platform 205 as described above.

Although illustrated as LED strips, indicators 201 on the patient platform 205 can embody other forms. For example, other types of visual and audible indicators 201 can be used. Further, the principles described above with regard to the indicators 201 on the adjustable arm supports 203 may also be applied to the indicators 201 on the patient platform 205. For example, in place of LED light strips, individual LEDs or other light sources can be used, the indicators 201 can comprise one or more screens, the indicators 201 can be configured to direct light in desired directions, the indicators 201 can be individually controllable so as to provide different zones, etc.

FIGS. 21A and 21B are intended to provide examples of placement locations for indicators 201 on the patient platform 205. The illustrated embodiments are not intended to be limiting and other locations and placements for the indicators 201 on the patient platform 205 are also possible. In the alternative, or in addition, other types of combinations indicators 201 may be placed on one or more portions of the patient platform 205.

C. Indicator Function.

As mentioned above, the indicators 201 described above can be configured to communicate information about the robotic medical system to users. Such information can comprise state or identity information for the system. As used herein, "state information" refers broadly to any information indicative of a state, status, or condition of the robotic medical system or a component thereof. "Identity information" is also used broadly to refer to information that can be used to identify a component of a robotic medical system. Examples of state and identity information are provided and discussed below. Other functions and uses of the indicators 201 are also described below.

As shown in the previously described examples, in some embodiments, the indicators 201 can comprise visual indicators. As noted above, visual indicators can comprise lights positioned on the robotic medical system. Visual indicators 201 configured as lights can be configured to serve one or more purposes as described below. For example, visual indicators 201 can be configured to provide illumination in the operating room. In many cases, robotic medical procedures are performed in darkened operating rooms so as to facilitate remote viewing of the robotically controlled instruments on a screen or console. While low light facilitates remote viewing of the robotic medical procedure, sterile users directly interacting with the patient or the robotic medical system can have difficulty seeing. The visual indicators 201 can provide illumination around the robotic medical system to improve visibility for those users. In some embodiments, the illumination provided by the indicators 201 can be oriented to illuminate a region below and around the patient platform 201. This may help users in proximity to the robotic system to see while minimizing any negative impact on remote viewers. In some embodiments, visual indicators can direct light towards the ground 219 as described above with reference to FIGS. 23B and 24.

Figure 27A:
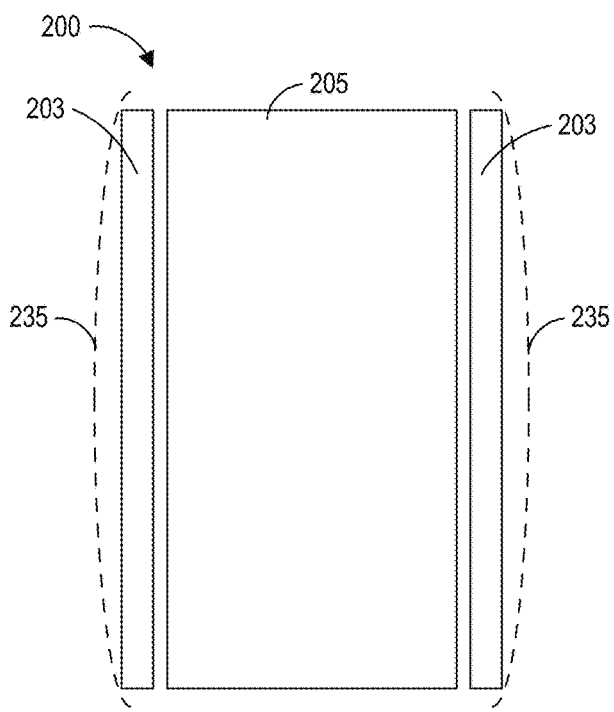
FIG. 27A illustrates a top view of an embodiment of a robotic medical system including functional indicators configured to provide mood lighting around the system.
Figure 27B:
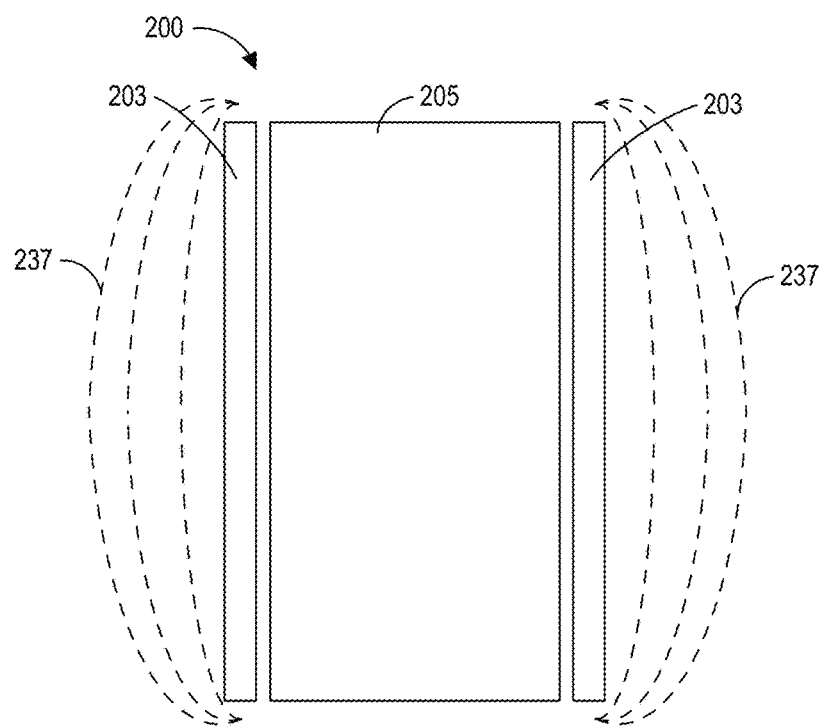
FIG. 27B illustrates a top view of an embodiment of a robotic medical system including functional indicators configured to provide an indication of a keep out zone around the system.

FIGS. 27A and 27B are top views of an embodiment of the robotic medical system 200 illustrating additional functionality that can be provided by visual indicators 201. In these figures, only the patient platform 205 and the adjustable arm supports 203 are illustrated. Additional features, such as robotic arms 207 have been omitted for clarity. The adjustable arm supports 203 and/or the patient platform 205 (or other components of the system 200) can include visual indicators 201 configured as described above. The visual indicators 201 are not pictured in FIGS. 27A and 27B, but approximate areas of illumination provided by the visual indicators 201 are illustrated using dashed lines. In some embodiments, the areas of illumination are regions on the ground that are illuminated by the visual indicators 201.

As shown in FIG. 27A, in some embodiments, visual indicators 201 can be configured to provide an area of illumination 235 positioned generally around the patient platform 205. The area of illumination 235 can be provided, for example, by visual indicators 201 that are configured to direct light substantially downward below the adjustable arm supports 203 and patient platform 205. Examples of such visual indicators 201 are shown on the lower surface 215 of the adjustable arm supports 203 of FIGS. 23B and 24. Other locations for visual indicators 201 configured to direct light downward are also possible. In some embodiments, the area of illumination 235 can provide "mood" lighting for the system 200. Such mood lighting can provide an elevated user experience. In some embodiments, the color of the mood lighting can be customized. For example, a surgeon can select a desired color of the mood lighting. The mood lighting may also facilitate visualization of the region below and around the patient platform 205.

FIG. 27B illustrates that, in some embodiments, the visual indicators 201 can be configured to provide a larger area of illumination 237 around the system 200. The larger area of illumination 237 can be provided, for example, by visual indicators 201 that are configured to direct light outwardly and downward below the adjustable arm supports 203 and patient platform 205. Examples of such visual indicators 201 are shown on the outer surface 209 of the adjustable arm supports 203 of FIGS. 23B and 24. Other locations for visual indicators 210 configured to direct light outwardly and downward are also possible. A larger area of illumination 237 can further improve visibility around the system 200.

In some embodiments, the area of illumination 237 can be configured to indicate a "keep out zone" in order to improve the safety of those users located around the patient platform 205. As noted previously, the system 200 may comprise one or more robotically moveable components, such as the adjustable arm supports 203 and/or robotic arms 207. In some embodiments, when the adjustable arm supports 203 and/or robotic arms 207 are about to move and/or during movement, the visual indicators 201 can provide an area of illumination 237 that corresponds to an area through which (or above which) the components will move. The area of illumination 237 can provide an indication to users in the area to keep clear of that area to avoid unintentional contact with the system. In some embodiments, for example, the area of illumination 237 can be provided in a specific color indicative of the keep out zone. For example, the area of illumination 237 can be illuminated in red. In another example, the area of illumination 237 can flash to attract the users' attention, while also indicating the keep out zone.

The areas of illumination 235, 237 shown in FIGS. 27A and 27B, may be approximate. For example, the boundaries of the illumination may not be clearly defined (e.g., through the use of generally diffuse light sources). In other embodiments, the areas of illumination 235, 237 shown in FIGS. 27A and 27B, may be definite, for example, with boundaries of the illumination may that are clearly defined (e.g., through the use of crisp or focused light sources). In some embodiments, to provide well defined boundaries, the indicators 201 may comprise lasers configured to project clearly onto the floor, In some embodiments, the visual indicators 201 can provide different types of illumination based on different functions of the system. For example, in the embodiments shown in FIGS. 27A and 27B, for a first function (e.g., the mood lighting as shown in FIG. 27A), the visual indicators 201 can illuminate at a first intensity (e.g., a lower intensity), while for a second function (e.g., the "keep out zone" lighting as shown in FIG. 27B), the visual indicators 201 can illuminate at a greater intensity. In addition, in some embodiments, for the first function, the visual indicators 201 can provide a constant light, while for the second function, the visual indicators 201 can provide a non-constant light that flashes, blinks, or otherwise has variable intensity. The visual indicators 201 can also incorporate different color lights to signify different functions.

In other embodiments, the first function (e.g., the mood lighting) can be provided by a first visual indicator 201 and the second function (e.g., the keep out zone lighting) can be provided by a second visual indicator 201. For example, the first function can be provided with the visual indicator 201 on the bottom or lower surface 215 of the adjustable arm support 203 in FIGS. 23B and 24, and the second function can be provided with the visual indicator 201 on the outer surface 209 of the adjustable arm support 203 in FIGS. 23B and 24. Configuring different visual indicators 201 for different functions can allow the visual indicators to provide both functions at the same time.

As described above with reference to FIG. 25, indicators 201 can be configured with independently configurable segments or zones. Activating (e.g., lighting up) indicators 201 within certain zones can provide several useful functions. In some embodiments, visual indicators 201 can be provided whereby different segments or zones of the visual indicators 201 light up depending on the purpose of the communication. FIGS. 28A-28D illustrate various functionality that can be provided by independently activating different zones or segments of the indicators 201.

Figure 28A:
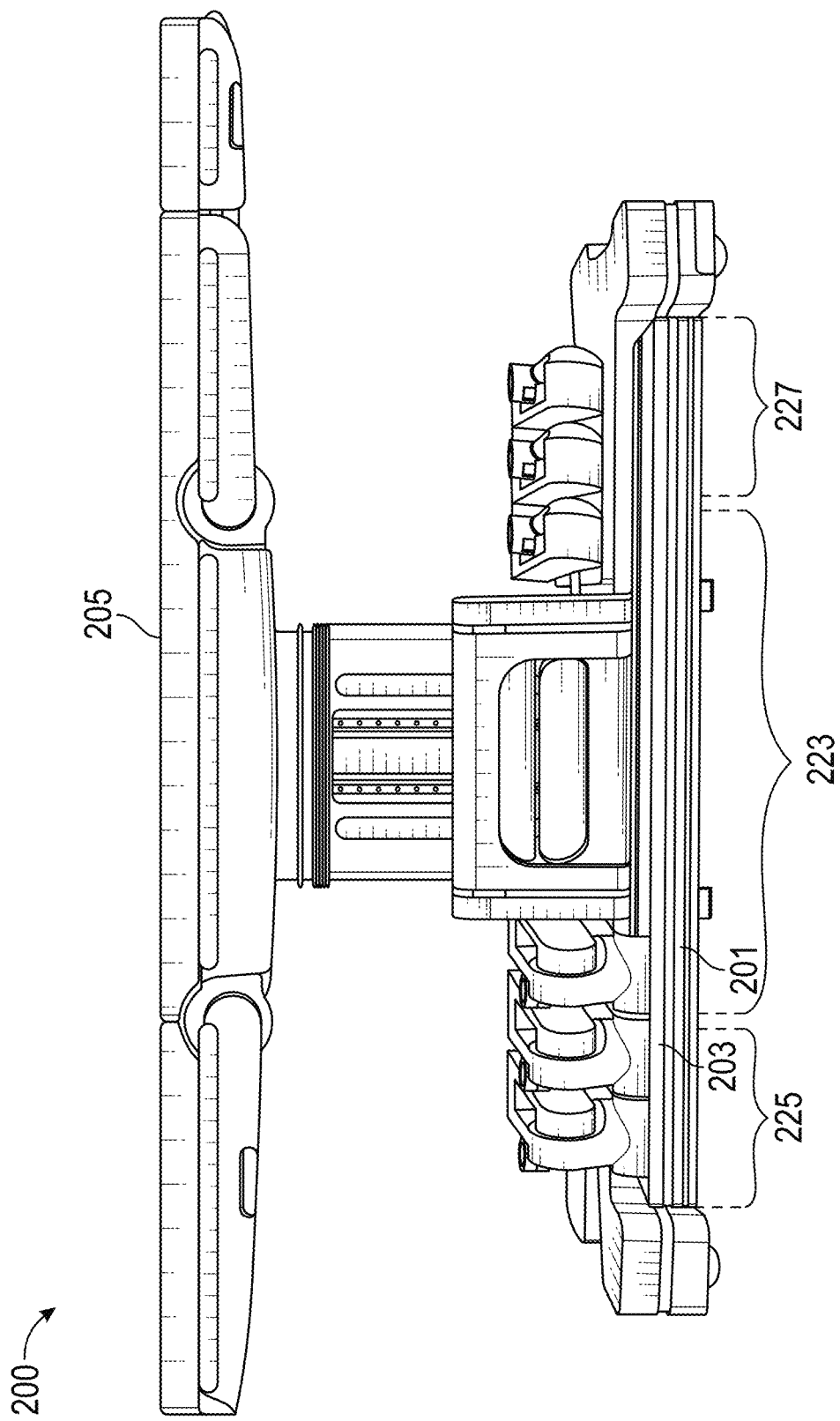
FIG. 28A illustrates a side view of an embodiment of a robotic medical system including functional indicators on an adjustable arm support configured to provide an indication of motion of the adjustable arm support.

FIG. 28A illustrates a side view of the system 200 with the adjustable arm support 203 in a storage configuration below the patient platform 205. In the illustrated embodiment, the adjustable arm support 203 includes a visual indicator 201 configured as an LED strip having a center zone 223 and two end zones 225, 227 as described above with reference to FIG. 25. In some embodiments, with the robotic system 200 in a first state or configuration, the three zones 223, 225, 227 of the visual indicator 201 (or combinations of the zones) can light up as a warning during deployment and stowing motion.

Figure 28B:
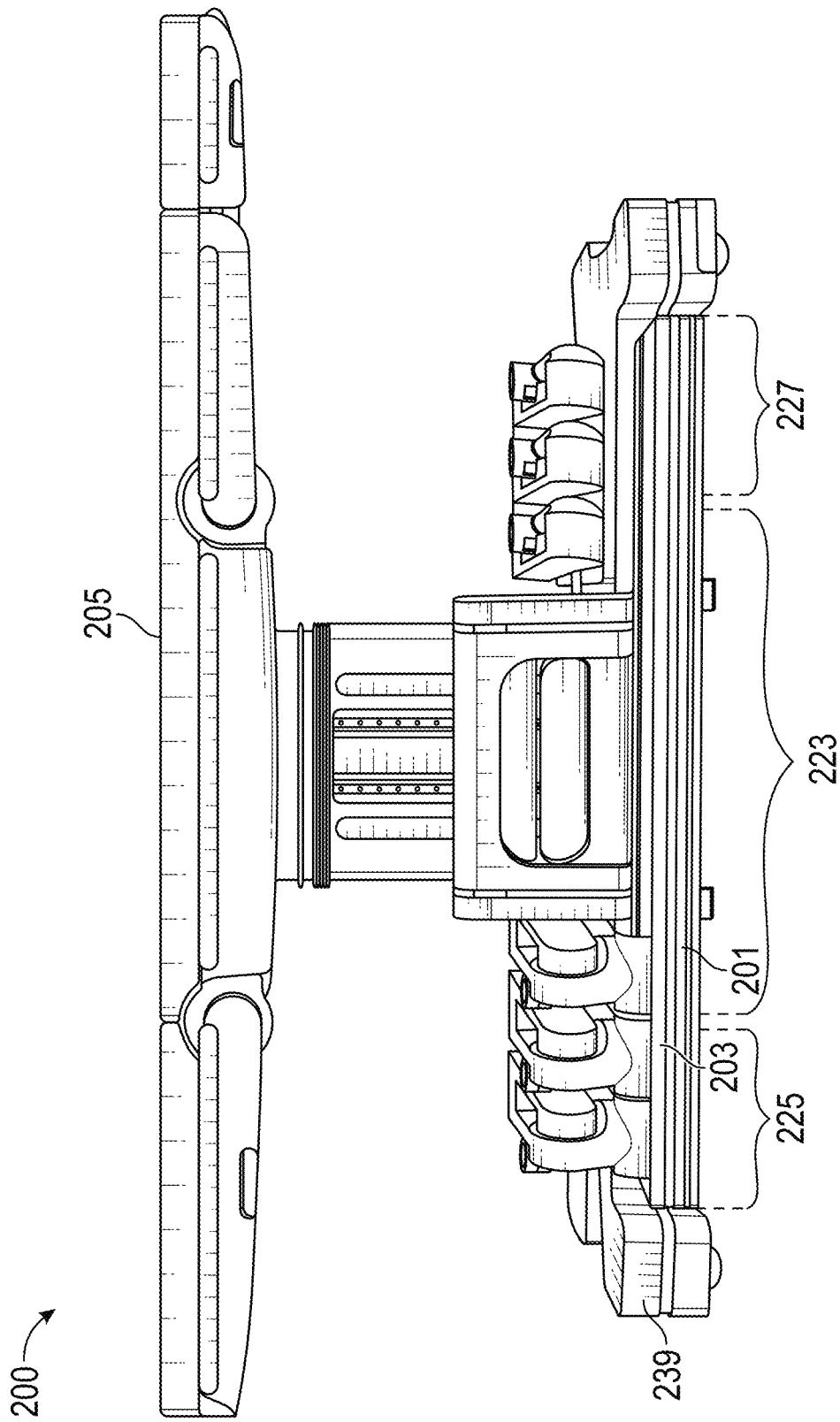
FIG. 28B illustrates a side view of an embodiment of a robotic medical system including functional indicators on an adjustable arm support configured to provide an indication of possible pinching due to motion of the system.

FIG. 28B illustrates that, with the robotic system 200 in a second state or configuration, different segments of the light strip can light up to highlight pinching dangers or warnings. For example, as illustrated, end zones 225, 227 can be activated to indicate a pinching danger between the ends of the adjustable arm support 203 and a base 239 of the system 200. In some embodiments, different color lights, flashing patterns, and/or different illumination intensity patterns can also be used on the different zones 225, 223, 227 of the visual indicator to indicate different functionality. For example, during a stowing motion, all three zones 223, 225, 227 can illuminate, with the end zones 225, 227 providing a different color or illumination pattern to indicate a pinching danger. As another example, visual indicators 201 can be used to minimize or reduce a trip hazard and/or to facilitate prompt discovery of any buttons or plugs located at or around the base of the patient platform. Such buttons may include, but are not limited, to actuators required in an emergency scenario. For example, portions of the indicators 201 corresponding to the locations of the buttons or plugs can light up in order to warn users in the area of their presence and/or to help the users find them more easily.

Figure 28C:
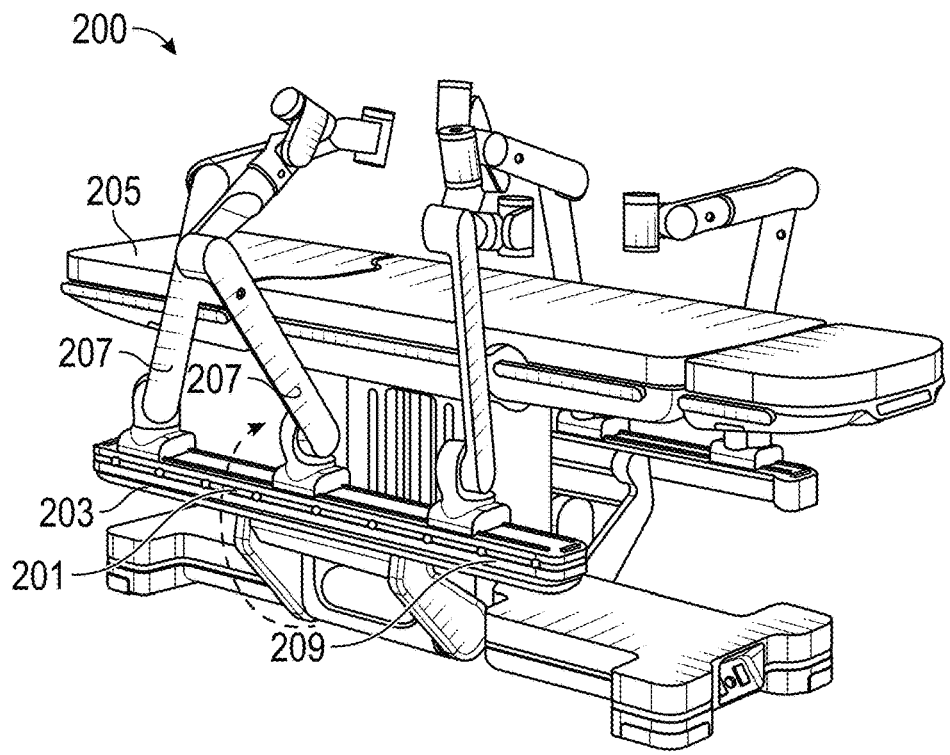
FIG. 28C is a perspective view of an embodiment of a robotic medical system including functional indicators on an adjustable arm support configured to provide an indication of a sweeping motion of the adjustable arm support.

FIG. 28C illustrates a perspective view of the system 200, including the adjustable arm supports 203, a plurality of robotic arms 207, and the patient platform 205. In the illustrated embodiment, a visual indicator 201 is provided along the outer surface 209 of the adjustable arm support 203. As described above with reference to FIGS. 12-14, the adjustable arm support 203 can be configured for a wide variety of motions. FIG. 28C illustrates an example sweeping motion (illustrated with the dashed arrow), wherein the adjustable arm support 203 is swept upward. This motion may be used, for example, to move the robotic arms 207 into position for a robotic medical procedure. During this movement state, the visual indicator 201 (or portions thereof, including combinations or patterns of the portions) may light up along its length to provide an indication to surrounding users of this movement.

Figure 28D:
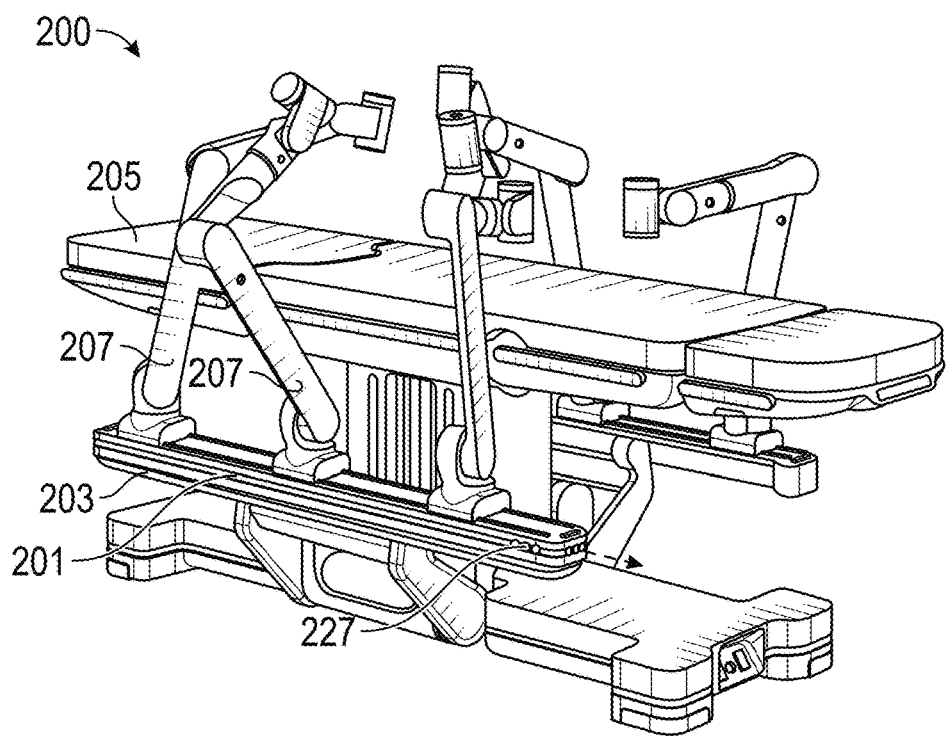
FIG. 28D is a perspective view of an embodiment of a robotic medical system including functional indicators on an adjustable arm support configured to provide an indication of translational motion of the adjustable arm support.

FIG. 28D illustrates another motion of the adjustable arm support 203 wherein the adjustable arm support 203 translates relative to the patient platform 205 (illustrated with the dashed arrow). As shown in FIG. 28D, during this movement state, an end zone 227 of the visual indicator may be activated to indicate the direction of motion of the adjustable arm support. In the illustrated embodiment, the end zone 227 wraps around the end of the adjustable arm support 203. This configuration can allow users standing in front of the patient platform to see the indication. In some embodiments, a moving pattern of lights along the adjustable arm support 203 may also provide an indication of a translational movement of the adjustable arm support 203.

Figure 29A:
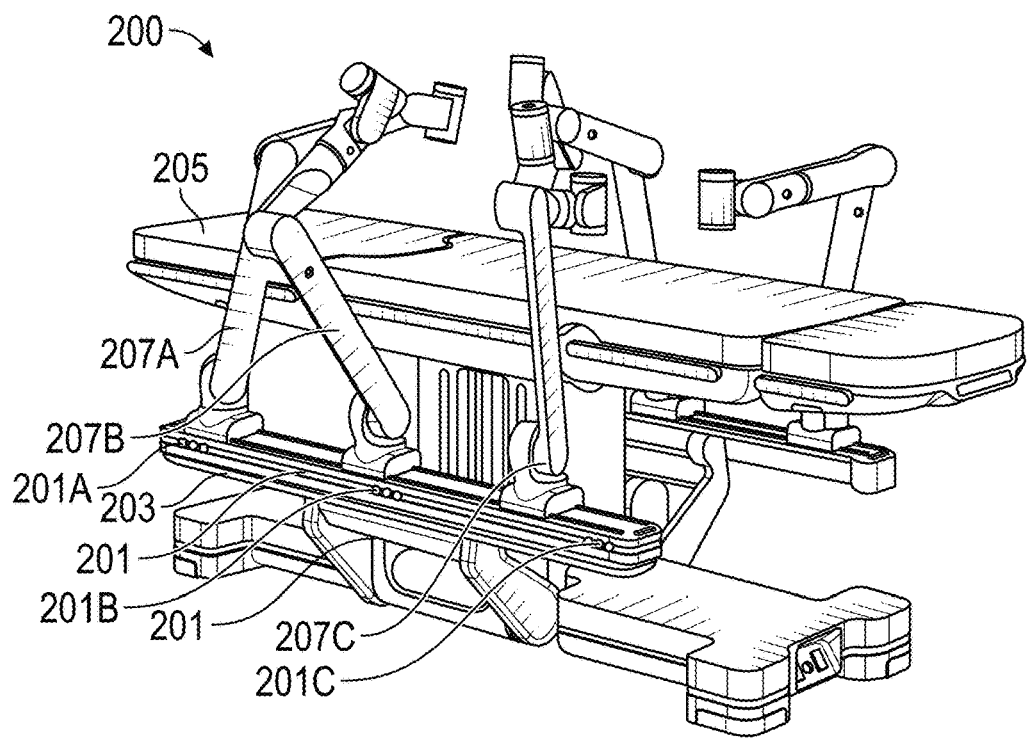
FIG. 29A is a perspective view of an embodiment of a robotic medical system including functional indicators on an adjustable arm support configured to provide identity information associated with robotic arms of the system.

The indicators 201 can also be configured to provide identity information for components of the robotic medical system 200. FIG. 29A, for example, illustrates an embodiment of the robotic medical system 200, wherein the indicators 201 are configured to provide identity information for the robotic arms 207. In FIG. 29A, the system 200 comprises three robotic arms 207A, 207B, 207C mounted on an adjustable arm support 203. As illustrated, the adjustable arm support 203 comprises an indicator 201 configured as an LED strip as described above. Indicator regions 201A, 201B, 201C of the indicator 201 can be illuminated to identify each of the robotic arms 207A, 207B, 207C. For example, a first region 201A can illuminate in a first color to identify the first robotic arm 207A. The first region 201A can be, for example, a portion of the indicator 201 in proximity to a base of the first robotic arm 207A. Similarly, a second region 201B can illuminate in a second color to identify the second robotic arm 207B. The second region 201B can be, for example, a portion of the indicator 201 in proximity to a base of the second robotic arm 207B. A third region 201C can illuminate in a third color to identify the third robotic arm 207C. The third region 201C can be, for example, a portion of the indicator 201 in proximity to a base of the third robotic arm 207C.

In this way, users can identify each of the robotic arms 207A, 207B, 207C by referring to the first, second, and third colors respectively. The first, second, and third colors may also be visible to a user that is controlling the robotic system 200 (e.g., a surgeon). The surgeon or user that is controlling the robotic system 200 is often not sterile, and thus is unable to interact directly with the robotic system 200 without scrubbing in, which can be a time consuming process. Still, during a robotic system, the surgeon may desire to have one or more components of the robotic system adjusted. The surgeon can refer to the first, second, and third colors to direct sterile users to the correct components of the robotic system 200.

Although described with reference to colors, the indicator 201 and indicator regions 201A, 201B, 201C can be configured to display identity information in different ways. For example, in some embodiments, the indicator 201 and indicator regions 201A, 201B, 201C can be configured to display identity via different patterns of illumination, changes in light intensity, sound, etc. In embodiments wherein the indicator 201 is configured as a screen (e.g., as shown in FIG. 22D), identity information can be displayed through text on the screen. For example, the indicator regions 201A, 201B, 201C associated with robotic arms 207A, 207B, 207C can display "arm 1," "arm 2," and "arm 3," for example. Additionally, although identity information has been described above with reference to robotic arms 207, identity information can be communicated with the indicator 201 for other components of the robotic system 200. For example, identity information can be related to medical instruments connected to the robotic arms 207, the adjustable arm supports 203, the patient, the patient platform 205, etc. Additionally, identity information can be provided on indicators 201 provided elsewhere on the robotic system 200, such as on indicators 201 on the patient platform 205.

Figure 29B:
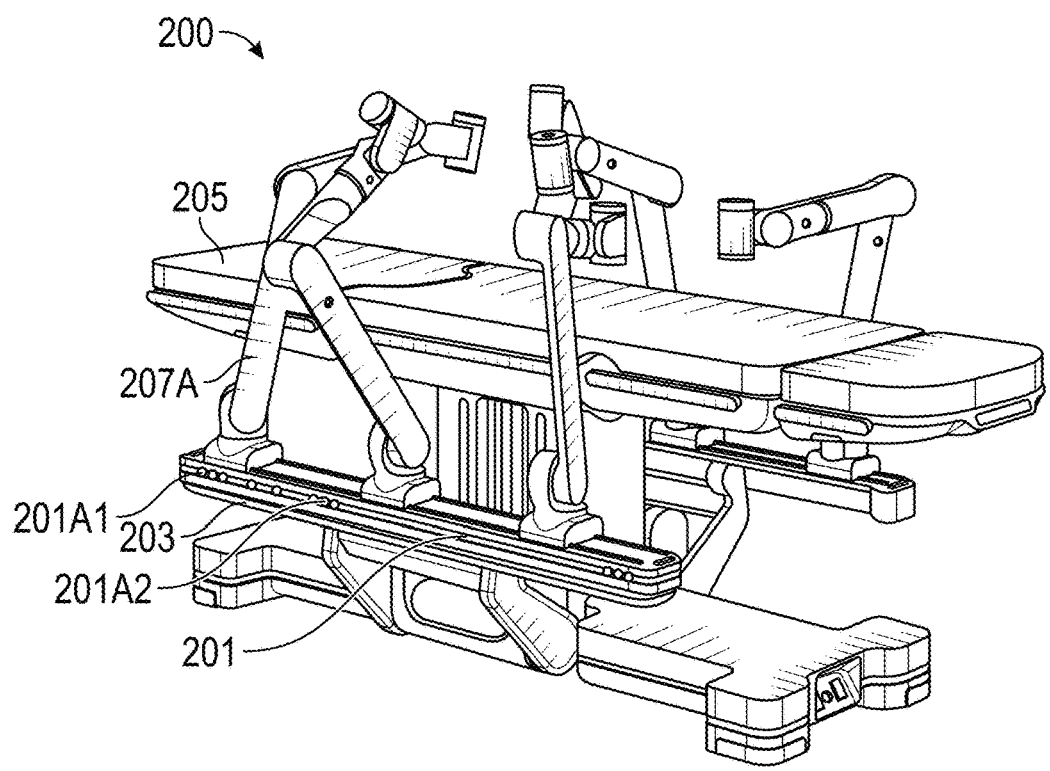
FIG. 29B is a perspective view of an embodiment of a robotic medical system including functional indicators on an adjustable arm support configured to provide movement information associated with movement of the robotic arms of the system along the adjustable arm support.

FIG. 29B is a perspective view of an embodiment of the robotic medical system 200 illustrating that the indicator 201 can be configured to provide an indication related to movement of robotic arms 207. As described above, in some embodiments, the robotic arms 207 may be movably mounted on the adjustable arm support 203. For example, a base of the robotic arm 207 can translate along the adjustable arm support 203. During this motion, there can be a risk of inadvertent contact between the robotic arm 207 and users in the vicinity. FIG. 29B illustrates that the indicator 201 can be configured to provide an indication of the motion of the robotic arm 207 to alert users to the motion of the arm.

For example, in FIG. 29B, the robotic arm 207 is (or is about to move) from a first location to a second location in the direction illustrated with the dashed arrow. A first indicator region 201A1 of the indicator 201 can indicate the current location of the robotic arm 207 and a second indicator region 201A2 can show the final position of the robotic arm 207. In some embodiments, a path between the first indicator region 201A1 and the second indicator region 201A2 can also be shown. Other methods for illustrating movement of the robotic arms 207 can also be used. Further, motion information for other components of the robotic system 200 can be provided with the indicators 201. As shown and described, in some embodiments, the indicators 201 can advantageously be configured to provide lighting that is capable of dynamically shifting along a length of the adjustable arm support 203 and/or patient platform 205 to track the movable robotic arms 207. For example, in the embodiment illustrated in FIG. 29A, the indicator 201 can comprise lights that can illuminate on the adjustable arm support 203 immediately adjacent to respective robotic arms 207, and, as the robotic arms 207 move, the lights can shift such they follow the position of the movable robotic arms 207, as shown in FIG. 29B.

In some embodiments, indicators 201 may be configured to provide an indication of a collision between components of the system, such as a collision between two robotic arms. For example, if two robotic arms 207 collide, indicators on the arm can be activated such that the collision can quickly and easily be identified.

In some embodiments, indicators 201 provide state information about medical instruments, such as medical instruments connected to the robotic arms 207. For example, indicators 201 can provide an indication that the system 200 is in an instrument docking state or that an instrument has been successfully docked to a robotic arm.

In some embodiments, the robotic systems can include torque sensors in or associated with the arms such that any collision can immediately trigger an emergency stop of the arm motion. In some embodiment, the system can be designed such that a deployment path or footprint size of the arms designed such that footprint increase is kept to a minimum. In some embodiments, audible indicators are configured to provide sound alarms while arms are deploying to alert everyone in the room to stop what they are doing and pay attention to the arms. In some embodiments, audible indicators are configured to provide vocal notifications from the system. For example, an audible indicator may state, "Attention—arms are deploying. Please step away from surgical bed." Different variations and combinations of indicators may be implemented depending on the particular application or medical procedure.

3. Implementing Systems and Terminology.

Implementations disclosed herein provide systems, methods and apparatus for functional lighting for robotic medical systems.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

Any phrases referencing specific computer-implemented processes/functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic medical system, comprising:
   a patient platform configured to support a patient during a robotic medical procedure;
   a column supporting the patient platform;
   an arm support coupled to the column;
   at least one robotic arm coupled to the arm support and configured to move along a path along the arm support; and
   an indicator positioned on the arm support, wherein the indicator comprises a plurality of independently controlled segments arranged along the path along the arm support, wherein the indicator is configured to indicate state or identity information of the at least one robotic arm, and wherein the indicator is configured to dynamically activate different zones along the path to track movement of the at least one robotic arm along the path.

2. The robotic medical system of claim 1, wherein the arm support comprises an adjustable arm support configured to move the at least one robotic arm relative to the patient platform.

3. The robotic medical system of claim 1, wherein the at least one robotic arm is configured to move from a stowed position below the patient platform to a deployed position wherein at least a portion of the at least one robotic arm is positioned above the patient platform, and wherein the indicator is configured to indicate movement of the at least one robotic arm from the stowed position to the deployed position.

4. The robotic medical system of claim 1, wherein the arm support comprises a bar extending along an axis between a first end and a second end, and wherein the at least one robotic arm is movably mounted to the bar such that the at least one robotic arm can translate along the bar.

5. The robotic medical system of claim 4, wherein the indicator comprises a visual indicator positioned on at least one of a top side, an outer side, an inner side, and a bottom side of the bar.

6. The robotic medical system of claim 1, wherein the indicator comprises a strip of light emitting diodes (LEDs) extending along the path.

7. The robotic medical system of claim 1, wherein the indicator is configured to indicate a direction of movement of the at least one robotic arm along the arm support.

8. The robotic medical system of claim 1, wherein the at least one robotic arm comprises a plurality of robotic arms coupled to the arm support, wherein each of the robotic arms is configured to move along the path along the arm support, wherein each of the independently controlled segments is configured to identify a respective one of the robotic arms having a base in proximity to that segment.

9. The robotic medical system of claim 1, wherein the indicator is configured to indicate first state information and second state information, wherein the first state information comprises at least one of: a stand by state, a powered state, an active state, a ready state, an error state and an emergency stop state.

10. The robotic medical system of claim 1, wherein the indicator is a visual indicator configured to illuminate a zone around the system indicative of an area through which the arm support will move to provide a visual indication of a zone of danger.

11. A robotic medical system, comprising:
    a surgical table comprising a base, a column, and a patient platform supported by the column;
    an arm support coupled to the surgical table;

a plurality of robotic arms coupled to the arm support, wherein each of the robotic arms has a base configured to move along a path along the arm support; and a visual indicator comprising a plurality of independently controlled lights positioned on the arm support and arranged along the path, wherein a pattern of illumination of the plurality of lights is configured to change upon movement of the plurality of robotic arms relative to the plurality of lights.

12. The robotic medical system of claim 11, wherein:
the plurality of lights comprises a first light and a second light;
the plurality of robotic arms comprises a first robotic arm and a second robotic arm;
the first light is configured to identify the first robotic arm when a base of the first robotic arm is in proximity to the first light; and
the second light is configured to identify the second robotic arm when a base of the second robotic arm is in proximity to the second light.

13. The robotic medical system of claim 11, wherein, when a first robotic arm of the plurality of robotic arms is moving or is about to move from a first location to a second location along the arm support, a first light of the plurality of lights located at the first location is configured to illuminate to indicate the first location and a second light of the plurality of lights located at the second location is configured to illuminate to indicate the second location.

14. A robotic medical system, comprising:
a patient platform configured to support a patient during a robotic medical procedure;
a column supporting the patient platform;
an arm support coupled to the column, wherein the arm support comprises a bar extending along an axis between a first end and a second end;
at least one robotic arm coupled to the arm support and configured to move along a path along the arm support, wherein the at least one robotic arm is movably mounted to the bar such that the at least one robotic arm can translate along the bar; and
an indicator positioned on the arm support, wherein the indicator comprises a plurality of independently controlled segments arranged along the path along the arm support, wherein the indicator is configured to indicate state or identity information of the at least one robotic arm, wherein the indicator comprises a visual indicator positioned on at least one of a top side, an outer side, an inner side, and a bottom side of the bar, and wherein the visual indicator extends onto the first end and the second end of the bar.

15. A robotic medical system, comprising:
a patient platform configured to support a patient during a robotic medical procedure;
a column supporting the patient platform;
an arm support coupled to the column;
at least one robotic arm coupled to the arm support and configured to move along a path along the arm support; and
an indicator positioned on the arm support, wherein the indicator comprises a plurality of independently controlled segments arranged along the path along the arm support, wherein the indicator is configured to indicate state or identity information of the at least one robotic arm, and wherein the indicator is configured to indicate a direction of movement of the arm support.

16. The robotic medical system of claim 15, wherein the direction of movement comprises at least one of a sweeping movement or a translating movement of the arm support.

17. A robotic medical system, comprising:
a patient platform configured to support a patient during a robotic medical procedure;
a column supporting the patient platform;
an arm support coupled to the column;
at least one robotic arm coupled to the arm support and configured to move along a path along the arm support; and
an indicator positioned on the arm support, wherein the indicator comprises a plurality of independently controlled segments arranged along the path along the arm support, wherein the indicator is configured to indicate state or identity information of the at least one robotic arm, wherein the indicator is configured to indicate first state information and second state information, wherein the first state information comprises at least one of: a stand by state, a powered state, an active state, a ready state, an error state and an emergency stop state, wherein the second state information is configured to indicate movement of the arm support.

18. The robotic medical system of claim 17, wherein the indicator is configured to indicate the first state information and the second state information concurrently.

* * * * *